US012672800B2

(12) United States Patent
Facchinetti et al.

(10) Patent No.: US 12,672,800 B2
(45) Date of Patent: Jul. 7, 2026

(54) ACCURACY CONTINUOUS GLUCOSE MONITORING METHOD, SYSTEM, AND DEVICE

(71) Applicant: UNIVERSITY OF VIRGINIA PATENT FOUNDATION, Charlottesville, VA (US)

(72) Inventors: Andrea Facchinetti, Padua (IT); Giovanni Sparacino, Padua (IT); Claudio Cobelli, Padua (IT); Boris Kovatchev, Padua (IT)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 1191 days.

(21) Appl. No.: 17/132,604

(22) Filed: Dec. 23, 2020

(65) Prior Publication Data
US 2021/0113122 A1 Apr. 22, 2021

Related U.S. Application Data

(63) Continuation of application No. 15/510,878, filed as application No. PCT/US2015/045340 on Aug. 14, 2015, now Pat. No. 10,881,334.
(Continued)

(51) Int. Cl.
*A61B 5/145* (2006.01)
*A61B 5/00* (2006.01)
(Continued)

(52) U.S. Cl.
CPC .......... *A61B 5/14532* (2013.01); *A61B 5/725* (2013.01); *A61B 5/7275* (2013.01);
(Continued)

(58) Field of Classification Search
CPC ... A61B 5/14532; A61B 5/725; A61B 5/7275; A61B 5/1495; G16H 40/60; G16H 50/50; G16H 40/40
See application file for complete search history.

(56) References Cited

U.S. PATENT DOCUMENTS

| | | | |
|---|---|---|---|
| 6,804,551 B2 | 10/2004 | Griffin et al. | |
| 6,923,763 B1 | 8/2005 | Kovatchev et al. | |

(Continued)

FOREIGN PATENT DOCUMENTS

| | | |
|---|---|---|
| EP | 3179914 A1 | 6/2017 |
| EP | 3179914 A4 | 4/2018 |

(Continued)

OTHER PUBLICATIONS

Andrew "Bayesian statistics: What's it all about?" (Year: 2016).*
(Continued)

*Primary Examiner* — Christian Jang
(74) *Attorney, Agent, or Firm* — Buchanan Ingersoll & Rooney PC

(57) ABSTRACT

A method, system, and device for improving the accuracy of a continuous glucose monitoring sensor by estimating a CGM signal at a time t+PH using a value of CGM at time t, using a real-time short-time glucose prediction horizon to estimate the real time denoised CGM value with a noise estimation algorithm.

17 Claims, 13 Drawing Sheets

Related U.S. Application Data

(60) Provisional application No. 62/037,133, filed on Aug. 14, 2014.

(51) Int. Cl.

| | |
|---|---|
| *A61B 5/1495* | (2006.01) |
| *G16H 40/40* | (2018.01) |
| *G16H 40/60* | (2018.01) |
| *G16H 50/50* | (2018.01) |

(52) U.S. Cl.
CPC ............. *G16H 40/40* (2018.01); *G16H 40/60* (2018.01); *G16H 50/50* (2018.01); *A61B 5/1495* (2013.01)

(56) References Cited

U.S. PATENT DOCUMENTS

| | | | |
|---|---|---|---|
| 7,025,425 | B2 | 4/2006 | Kovatchev et al. |
| 7,403,814 | B2 | 7/2008 | Cox et al. |
| 7,761,144 | B2 | 7/2010 | Cox et al. |
| 7,806,886 | B2 | 10/2010 | Kanderian et al. |
| 7,815,569 | B2 | 10/2010 | Kovatchev et al. |
| 7,874,985 | B2 | 1/2011 | Kovatchev et al. |
| 8,135,548 | B2 | 3/2012 | Breton et al. |
| 8,340,752 | B2 | 12/2012 | Cox et al. |
| 8,538,703 | B2 | 9/2013 | Kovatchev et al. |
| 8,562,587 | B2 | 10/2013 | Kovatchev et al. |
| 8,585,593 | B2 | 11/2013 | Kovatchev et al. |
| 8,718,958 | B2 | 5/2014 | Breton et al. |
| 10,881,334 | B2 * | 1/2021 | Facchinetti .......... A61B 5/7275 |
| 2002/0099282 | A1 * | 7/2002 | Knobbe ................. A61B 5/725 |
| | | | 600/365 |
| 2004/0167382 | A1 | 8/2004 | Gardner et al. |
| 2005/0203360 | A1 * | 9/2005 | Brauker ............... A61B 5/7275 |
| | | | 600/345 |
| 2008/0154513 | A1 | 6/2008 | Kovatchev et al. |
| 2008/0314395 | A1 | 12/2008 | Kovatchev et al. |
| 2009/0171589 | A1 | 7/2009 | Kovatchev |
| 2010/0057043 | A1 | 3/2010 | Kovatchev et al. |
| 2010/0179768 | A1 | 7/2010 | Kovatchev et al. |
| 2010/0198520 | A1 | 8/2010 | Breton et al. |
| 2011/0237917 | A1 * | 9/2011 | Roy ..................... A61B 5/1495 |
| | | | 702/19 |
| 2011/0264374 | A1 | 10/2011 | Johnson et al. |
| 2011/0264378 | A1 | 10/2011 | Breton et al. |
| 2011/0313680 | A1 | 12/2011 | Doyle et al. |
| 2012/0004512 | A1 | 1/2012 | Kovatchev et al. |
| 2012/0078067 | A1 | 3/2012 | Kovatchev et al. |
| 2012/0130698 | A1 | 5/2012 | Kovatchev et al. |
| 2012/0191361 | A1 | 7/2012 | Kovatchev et al. |
| 2012/0215087 | A1 | 8/2012 | Cobelli et al. |
| 2012/0245556 | A1 | 9/2012 | Kovatchev et al. |
| 2013/0079613 | A1 | 3/2013 | Kovatchev et al. |
| 2013/0116649 | A1 | 5/2013 | Breton et al. |
| 2014/0046159 | A1 | 2/2014 | Kovatchev et al. |
| 2014/0215239 | A1 | 7/2014 | Kovatchev et al. |
| 2014/0221966 | A1 | 8/2014 | Buckingham et al. |
| 2015/0018633 | A1 | 1/2015 | Kovachev et al. |
| 2016/0006446 | A1 * | 1/2016 | Wiberg ..................... H03L 7/24 |
| | | | 331/34 |

FOREIGN PATENT DOCUMENTS

| | | | |
|---|---|---|---|
| WO | 0113786 | A1 | 3/2001 |
| WO | 0172208 | A2 | 10/2001 |
| WO | 02067776 | A1 | 9/2002 |
| WO | 02091119 | A2 | 11/2002 |
| WO | 2004015539 | A2 | 2/2004 |
| WO | 2005089431 | A2 | 9/2005 |
| WO | 2005106017 | A2 | 11/2005 |
| WO | 2007027691 | A1 | 3/2007 |
| WO | 2007081853 | A2 | 7/2007 |
| WO | 2008052199 | A2 | 5/2008 |
| WO | 2008067284 | A2 | 6/2008 |
| WO | 2008157781 | A1 | 12/2008 |
| WO | 2009009528 | A2 | 1/2009 |
| WO | 2009026381 | A2 | 2/2009 |
| WO | 2010099313 | A1 | 9/2010 |
| WO | 2010138848 | A1 | 12/2010 |
| WO | 2010151834 | A1 | 12/2010 |
| WO | 2011028731 | A1 | 3/2011 |
| WO | 2011028925 | A1 | 3/2011 |
| WO | 2011112974 | A1 | 9/2011 |
| WO | 2011119832 | A1 | 9/2011 |
| WO | 2012178113 | A1 | 12/2012 |
| WO | 2012178134 | A2 | 12/2012 |
| WO | 2013032965 | A1 | 3/2013 |
| WO | 2014022864 | A1 | 2/2014 |
| WO | 2014130841 | A1 | 8/2014 |
| WO | 2015003124 | A2 | 1/2015 |
| WO | 2016025874 | A1 | 2/2016 |

OTHER PUBLICATIONS

Facchinetti, "An Online Self-Tunable Method to Denoise CGM Sensor Data". IEEE Transactions on Biomedical Engineering, vol. 57, No. 3, Mar. 2010 (Year: 2010).*

U.S. Appl. No. 29/467,039, Sep. 13, 2013.

Australian Office Action ("Examination report No. 1") issued on Sep. 29, 2017, by IP Australia in corresponding Australian Patent Application No. 2015301454. (4 pages).

Office Action (Examination Report No. 2) issued on Sep. 13, 2018, by the Australian Patent Office in corresponding Australian Patent Application No. 2015301454. (4 pages).

Office Action (Examination Report No. 2) issues Sep. 13, 2018 by the Australian Patent Office in corresponding Australian Patent Application No. 2015301545. (4 pages).

Office Action (Examination Report No. 1) issued on Nov. 28, 2019, by the Australian Patent Office in corresponding Australian Patent Application No. 2018236794. (5 pages).

Office Action (Communication) issued on Apr. 3, 2020, by the European Patent Office in corresponding European Patent Application No. 15832438.4. (3 pages).

Office Action (Communication pursuant to Rules 70(2) and 70a(2) EPC) issued on Mar. 29, 2018, by the European Patent Office in corresponding European Patent Application No. 15832438.4-1132. (1 page).

Facchinetti, Andrea, et al., "An Online Self-Tunable Method to Denoise CGM Sensor Data", IEEE Transactions on Biomedical Engineering, vol. 57, No. 3, Mar. 1, 2010, pp. 634-641.

International Preliminary Report on Patentability (PCT/IB373 issued on Feb. 14, 2017, by the U.S. Patent Office for International Application No. PCT/US2015/045340.

International Search Report (PCT/ISA/210) issued on Nov. 27, 2015, by the U.S. Patent Office as the International Searching Authority for International Application No. PCT/US2015/045340.

Written Opinion (PCT/ISA/237) issued on Nov. 27, 2015, by the U.S. Patent Office as the International Searching Authority for International Application No. PCT/US2015/045340.

Sparacino, G et al., "Smart Continuous Glucose Monitoring Sensors: On-Line Signal Processing Issues", Senors Jul. 12, 2010, pp. 6751-6772.

Office Action issued on Aug. 27, 2021, by the Canadian Patent Office in corresponding Canadian Patent Application No. 2,958,067. (4 pages).

Office Action (Examination Report No. 1) issued on Dec. 12, 2023, by the Australian Patent Office in corresponding Australian Patent Application No. 2023200213. (5 pages).

Office Action (Examination Report No. 1) issued on Jan. 15, 2022, by the Australian Patent Office in corresponding Australian Patent Application No. 2021200374. (5 pages).

Office Action (Notice of Acceptance) issued on May 28, 2024, by the Australian Patent Office in corresponding Australian Patent Application No. 2023200213. (3 pages).

(56)　　　　　　　References Cited

OTHER PUBLICATIONS

The extended European Search Report issued on Jun. 5, 2025, by the European Patent Office in corresponding European Application No. 24218061.0. (7 pages).

* cited by examiner

COMBINED P-EGA AND R-EGA RESULTS FOR ORIGINAL CGM

POINT ERROR - GRID ZONES

| ORIGINAL CGM VS. BG REFERENCES | HYPOGLYCEMIA | | | EUGLYCEMIA | | | HYPERGLYCEMIA | | | | |
|---|---|---|---|---|---|---|---|---|---|---|---|
| | A | D | E | A | B | C | A | B | C | D | E |
| A | 53.3% | 28.3% | 0.0% | 81.7% | 5.1% | 0.0% | 78.1% | 0.7% | 0.0% | 0.0% | 0.0% |
| B | 8.3% | 6.7% | 0.0% | 8.5% | 1.5% | 0.0% | 15.4% | 0.4% | 0.0% | 0.1% | 0.0% |
| uC | 0.0% | 0.0% | 0.0% | 0.0% | 0.0% | 0.0% | 0.6% | 0.0% | 0.0% | 0.0% | 0.0% |
| iC | 1.7% | 0.0% | 0.0% | 0.4% | 0.1% | 0.0% | 0.1% | 0.1% | 0.0% | 0.0% | 0.0% |
| uD | 0.0% | 0.0% | 0.0% | 0.3% | 0.6% | 0.0% | 1.6% | 0.2% | 0.0% | 0.0% | 0.0% |
| iD | 0.0% | 0.0% | 0.0% | 1.1% | 0.1% | 0.0% | 2.4% | 0.1% | 0.0% | 0.0% | 0.0% |
| uE | 0.0% | 1.7% | 0.0% | 0.3% | 0.1% | 0.0% | 0.1% | 0.0% | 0.0% | 0.0% | 0.0% |
| iE | 0.0% | 0.0% | 0.0% | 0.1% | 0.1% | 0.0% | 0.1% | 0.0% | 0.0% | 0.0% | 0.0% |

RATE ERROR - GRID ZONES

ACCURATE READINGS

BENIGN ERRORS

ERRONEOUS READINGS

FIG. 9

COMBINED P-EGA AND R-EGA RESULTS FOR ORIGINAL CGM_NEW WITH PH = 12 MINUTES

POINT ERROR - GRID ZONES

| CGM_NEW VS BG REFERENCES (PH = 12 MINS) | HYPOGLYCEMIA | | | EUGLYCEMIA | | | HYPERGLYCEMIA | | | | |
|---|---|---|---|---|---|---|---|---|---|---|---|
| | A | D | E | A | B | C | A | B | C | D | E |
| A | 68.3% | 13.3% | 0.0% | 76.2% | 4.4% | 0.0% | 74.0% | 0.3% | 0.0% | 0.0% | 0.0% |
| B | 8.7% | 5.0% | 0.0% | 12.3% | 2.1% | 0.0% | 18.1% | 0.3% | 0.0% | 0.0% | 0.0% |
| uC | 0.0% | 3.3% | 0.0% | 0.8% | 0.3% | 0.0% | 1.5% | 0.0% | 0.0% | 0.0% | 0.0% |
| IC | 1.7% | 0.0% | 0.0% | 1.0% | 0.3% | 0.0% | 0.6% | 0.3% | 0.0% | 0.0% | 0.0% |
| uD | 0.0% | 0.0% | 0.0% | 0.3% | 0.6% | 0.0% | 1.0% | 0.2% | 0.0% | 0.0% | 0.0% |
| ID | 0.0% | 0.0% | 0.0% | 0.7% | 0.1% | 0.0% | 2.2% | 0.1% | 0.0% | 0.0% | 0.0% |
| uE | 0.0% | 1.7% | 0.0% | 0.3% | 0.2% | 0.0% | 0.8% | 0.0% | 0.0% | 0.0% | 0.0% |
| IE | 68.3% | 13.3% | 0.0% | 76.2% | 4.4% | 0.0% | 74.0% | 0.3% | 0.0% | 0.0% | 0.0% |

RATE ERROR - GRID ZONES

ACCURATE READINGS    BENIGN ERRORS    ERRONEOUS READINGS

FIG. 10

COMBINED P-EGA AND R-EGA RESULTS FOR ORIGINAL CGMnew WITH INDIVIDUALIZED PH

POINT ERROR - GRID ZONES

| CGMnew VS BG REFERENCES (INDIVIDUALIZED PH) | HYPOGLYCEMIA | | | EUGLYCEMIA | | | HYPERGLYCEMIA | | | | |
|---|---|---|---|---|---|---|---|---|---|---|---|
| | A | D | E | A | B | C | A | B | C | D | E |
| A | 71.5% | 15.0% | 0.0% | 76.8% | 3.4% | 0.0% | 73.5% | 0.0% | 0.0% | 0.0% | 0.0% |
| B | 5.0% | 1.7% | 0.0% | 12.5% | 2.1% | 0.0% | 18.8% | 0.2% | 0.0% | 0.0% | 0.0% |
| uC | 0.0% | 1.7% | 0.0% | 0.8% | 0.3% | 0.0% | 1.8% | 0.0% | 0.0% | 0.0% | 0.0% |
| IC | 1.7% | 1.7% | 0.0% | 1.0% | 0.4% | 0.0% | 0.8% | 0.3% | 0.0% | 0.0% | 0.0% |
| uD | 0.0% | 0.0% | 0.0% | 0.5% | 0.7% | 0.0% | 0.9% | 0.2% | 0.0% | 0.0% | 0.0% |
| ID | 0.0% | 0.0% | 0.0% | 0.6% | 0.1% | 0.0% | 1.7% | 0.1% | 0.0% | 0.0% | 0.0% |
| uE | 0.0% | 1.7% | 0.0% | 0.3% | 0.1% | 0.0% | 0.9% | 0.0% | 0.0% | 0.0% | 0.0% |
| IE | 0.0% | 0.0% | 0.0% | 0.4% | 0.0% | 0.0% | 0.7% | 0.1% | 0.0% | 0.0% | 0.0% |

RATE ERROR - GRID ZONES

ACCURATE READINGS    BENIGN ERRORS    ERRONEOUS READINGS

*FIG. 11*

ACCURACY CONTINUOUS GLUCOSE MONITORING METHOD, SYSTEM, AND DEVICE

CROSS-REFERENCE TO RELATED APPLICATION AND CLAIM OF PRIORITY

This application claims priority under 35 U.S.C. 119(e) from U.S. Provisional Application Ser. No. 62/037,133 filed Aug. 14, 2014, which is incorporated herein by reference in its entirety.

FIELD

A method, system, and device for improving the accuracy of continuous glucose monitoring through short-time prediction. For example, the accuracy of a continuous monitoring sensor is improved.

BACKGROUND

The advent of continuous glucose monitoring (CGM) provided an improvement in the control and understanding of glucose levels in diabetic patients [1]. The quasi-continuous data stream allows collecting information about glucose variability, detection, and quantification of the duration of hypo- and hyper-glycemic events [2]. Clinically, the analysis of CGM data, either in real time or retrospective, is extremely useful in the management of diabetes [3, 4].

In terms of technology advancement, CGM sensors coupled with an insulin pump carry a promise for the design and development of artificial pancreas and automated closed-loop control [5-7]. Advisory devices, which suggest actions in real time, are also under investigation, e.g. the one developed for the DIAdvisor project [8]. The present inventors recognize that a crucial aspect for the success of these devices is the accuracy of the CGM sensors. Because CGM sensors measure interstitial glucose (IG) rather than blood glucose (BG) directly, the accuracy of CGM readings is suboptimal [9, 10].

To illustrate the problem, FIG. 1 shows an example of CGM time series (line), collected every minute using the Freestyle Navigator® (Abbott Diabetes Care, Alameda, CA), and compared to high frequently measured BG references, obtained every 15 minutes with YSI BG analyzer (YSI, Inc., Yellow Springs, OH). It is evident that the CGM trace diverges from the BG trace, both in terms of amplitude and delay. The difference, which is mostly evident during the rising and falling fronts, is typically attributed to the kinetics between BG and IG concentrations, which acts as a low-pass filter between the two sites [11, 12].

SUMMARY

Various objects and advantages of the preferred embodiments of the present invention will be appreciated based on this disclosure. According to the preferred embodiments, the present invention improves the accuracy of glucose monitoring sensors through short-time prediction.

As an exemplary embodiment of the invention, a method for improving the accuracy of a continuous glucose monitoring sensor (CGS) comprising or consisting of improving accuracy of CGM readings by reducing random noise and calibration errors using real-time short-time glucose prediction.

As a further exemplary embodiment of the invention, a method for improving the accuracy of a continuous glucose monitoring sensor (CGS) comprising or consisting of improving accuracy of CGM readings by reducing random noise and calibration errors using real-time short-time glucose prediction; with a prediction horizon (PH) of less than 20 minutes.

As an even further exemplary embodiment of the invention, a method for improving the accuracy of a continuous glucose monitoring sensor (CGS) comprising or consisting of improving accuracy of CGM readings by reducing random noise and calibration errors using real-time short-time glucose prediction; and compensating part of a delay introduced by low-pass nature of BG-to-IG kinetic system.

As yet another exemplary embodiment of the invention, a method for improving the accuracy of a continuous glucose monitoring sensor (CGS) comprising or consisting of improving accuracy of CGM readings by reducing random noise and calibration errors using real-time short-time glucose prediction; predicting a horizon PH of less than 20 minutes; and compensating part of a delay introduced by low-pass nature of BG-to-IG kinetic system.

As yet a further exemplary embodiment of the invention, a method for improving the accuracy of a continuous glucose monitoring sensor (CGS) comprising or consisting of improving accuracy of CGM readings by reducing random noise and calibration errors using real-time short-time glucose prediction; and substituting a current CGM value given in output by the sensors at time t, named CGM(t), with the glucose concentration predicted by an algorithm PH minutes ahead in time.

As an even further exemplary embodiment of the invention, a method for improving the accuracy of a continuous glucose monitoring sensor (CGS) comprising or consisting of improving accuracy of CGM readings by reducing random noise and calibration errors using real-time short-time glucose prediction; substituting a current CGM value given in output by the sensors at time t, named CGM(t), with the glucose concentration predicted by an algorithm PH minutes ahead in time, wherein the algorithm PH minutes ahead in time is $CGM_{NEW}(t)=CGM(t+PH|t)$.

As another exemplary embodiment of the invention, a method for improving the accuracy of a continuous glucose monitoring sensor (CGS) comprising or consisting of improving accuracy of CGM readings by reducing random noise and calibration errors using real-time short-time glucose prediction; substituting a current CGM value given in output by the sensors at time t, named CGM(t), with the glucose concentration predicted by an algorithm PH minutes ahead in time; and developing the algorithm in a stochastic context and implemented using a Kalman filter.

As a further exemplary embodiment of the invention, a method for improving the accuracy of a continuous glucose monitoring sensor (CGS) comprising or consisting of improving accuracy of CGM readings by reducing random noise and calibration errors using real-time short-time glucose prediction; and using CGM data only intended for real-time application.

As another further exemplary embodiment of the invention, a method for improving the accuracy of a continuous glucose monitoring sensor (CGS) comprising or consisting of improving accuracy of CGM readings by reducing random noise and calibration errors using real-time short-time glucose prediction; and denoising by using a Kalman filter (KF) coupled with a Bayesian smoothing criterion for the estimation of its unknown parameters.

As an exemplary embodiment of the invention, a system for improving the accuracy of a continuous glucose monitoring sensor comprising or consisting of a digital processor;

a continuous glucose monitoring (CGM) sensor in communication with the digital processor, the continuous glucose monitoring (CGM) sensor configured to generate a glucose signal; and a denoising module, configured to receive the glucose signal from the continuous glucose monitoring (CGM) sensor, and generate an improved accuracy CGM signal by reducing random noise and calibration errors using real-time short-time glucose prediction.

As another exemplary embodiment of the invention, a system for improving the accuracy of a continuous glucose monitoring sensor comprising or consisting of a digital processor; a continuous glucose monitoring (CGM) sensor in communication with the digital processor, the continuous glucose monitoring (CGM) sensor configured to generate a glucose signal; and a denoising module, configured to receive the glucose signal from the continuous glucose monitoring (CGM) sensor, and generate an improved accuracy CGM signal by reducing random noise and calibration errors using real-time short-time glucose prediction, wherein the denoising module is configured to predict a horizon PH of less than 20 minutes.

As a further exemplary embodiment of the invention, a system for improving the accuracy of a continuous glucose monitoring sensor comprising or consisting of a digital processor; a continuous glucose monitoring (CGM) sensor in communication with the digital processor, the continuous glucose monitoring (CGM) sensor configured to generate a glucose signal; and a denoising module, configured to receive the glucose signal from the continuous glucose monitoring (CGM) sensor, and generate an improved accuracy CGM signal by reducing random noise and calibration errors using real-time short-time glucose prediction, wherein the denoising module is configured to compensate part of a delay introduced by low-pass nature of BG-to-IG kinetic system.

As an even further exemplary embodiment of the invention, a system for improving the accuracy of a continuous glucose monitoring sensor comprising or consisting of a digital processor; a continuous glucose monitoring (CGM) sensor in communication with the digital processor, the continuous glucose monitoring (CGM) sensor configured to generate a glucose signal; and a denoising module, configured to receive the glucose signal from the continuous glucose monitoring (CGM) sensor, and generate an improved accuracy CGM signal by reducing random noise and calibration errors using real-time short-time glucose prediction, wherein the denoising module is configured to substitute a current CGM value given in output by the sensors at time t, named CGM(t), with the glucose concentration predicted by an algorithm PH minutes ahead in time.

As yet another exemplary embodiment of the invention, a system for improving the accuracy of a continuous glucose monitoring sensor comprising or consisting of a digital processor; a continuous glucose monitoring (CGM) sensor in communication with the digital processor, the continuous glucose monitoring (CGM) sensor configured to generate a glucose signal; and a denoising module, configured to receive the glucose signal from the continuous glucose monitoring (CGM) sensor, and generate an improved accuracy CGM signal by reducing random noise and calibration errors using real-time short-time glucose prediction, wherein the denoising module is configured to substitute a current CGM value given in output by the sensors at time t, named CGM(t), with the glucose concentration predicted by an algorithm PH minutes ahead in time, and wherein the algorithm PH minutes ahead in time is $CGM_{NEW}(t)=CGM(t+PH|t)$.

As yet a further exemplary embodiment of the invention, a system for improving the accuracy of a continuous glucose monitoring sensor comprising or consisting of a digital processor; a continuous glucose monitoring (CGM) sensor in communication with the digital processor, the continuous glucose monitoring (CGM) sensor configured to generate a glucose signal; and a denoising module, configured to receive the glucose signal from the continuous glucose monitoring (CGM) sensor, and generate an improved accuracy CGM signal by reducing random noise and calibration errors using real-time short-time glucose prediction, wherein the denoising module is configured to substitute a current CGM value given in output by the sensors at time t, named CGM(t), with the glucose concentration predicted by an algorithm PH minutes ahead in time, wherein the algorithm PH minutes ahead in time is $CGM_{NEW}(t)=CGM(t+PH|t)$, and wherein the algorithm is developed in a stochastic context and implemented using a Kalman filter.

As yet an even further exemplary embodiment of the invention, a system for improving the accuracy of a continuous glucose monitoring sensor comprising or consisting of a digital processor; a continuous glucose monitoring (CGM) sensor in communication with the digital processor, the continuous glucose monitoring (CGM) sensor configured to generate a glucose signal; and a denoising module, configured to receive the glucose signal from the continuous glucose monitoring (CGM) sensor, and generate an improved accuracy CGM signal by reducing random noise and calibration errors using real-time short-time glucose prediction, wherein the denoising module is configured to substitute a current CGM value given in output by the sensors at time t, named CGM(t), with the glucose concentration predicted by an algorithm PH minutes ahead in time, wherein the algorithm PH minutes ahead in time is $CGM_{NEW}(t)=CGM(t+PH|t)$, wherein the algorithm is developed in a stochastic context and implemented using a Kalman filter, and wherein the denoising algorithm uses CGM data only intended for real-time application.

Methods have been suggested to improve the accuracy of CGM readings by reducing random noise and calibration errors [13-17]. Accordingly, an aspect of an embodiment of the present invention method, system, and computer readable medium provides, but not limited thereto, using real-time short-time prediction (i.e. prediction with horizon less than 20 minutes) to improve the accuracy of CGM devices by compensating part of the delay introduced by the low-pass nature of the BG-to-IG kinetic system.

Continuous glucose monitoring (CGM) sensors assess blood glucose (BG) fluctuations indirectly—by measuring interstitial glucose (IG) concentration. However, IG and BG concentration time-series are different because of the existence of a BG-to-IG kinetics. The presence of the BG-to-IG dynamics affects the accuracy of CGM devices, in particular in the hypoglycemic range. For instance, the effect of the BG-to-IG dynamics is evident in the representative real dataset shown in FIG. 1, where BG samples (stars), obtained by a gold standard measurement technique by drawing a sample every 15 min, are compared with CGM measured in parallel through a commercial sensor device (line). CGM data appears to be delayed and slightly attenuated in amplitude with respect to BG.

An aspect of an embodiment of the present invention method, system, and computer readable medium provides, but not limited thereto, the use of real-time short-time glucose prediction (i.e. with prediction horizon PH of less than 20 minutes) as a solution to improve the accuracy of CGM devices. The core of the invention lies in substituting the current CGM value given in output by the sensors at time t, named CGM(t), with the glucose concentration predicted by a suitable algorithm PH minutes ahead in time, i.e. $CGM_{NE}w(t)=CGM(t+PH|t)$. In particular, the implementation of short-time prediction here illustrated presents the following important features: works in real-time, and can be either embedded in commercial CGM sensor or located in cascade. The proposed algorithm (and related method, technique, system, and computer readable medium) is robust and has many advantages (as discussed later in the text), because but not limited thereto, it is developed in a stochastic context and implemented using a Kalman filter. The procedure uses CGM data only and is intended for real-time application.

In order to demonstrate the effectiveness of the invention, it was tested by the present inventors retrospectively on 25 data sets consisting of Freestyle Navigator™ traces (1-min sampling) and reference BG time-series (15-min sampling) observed in parallel for up to 48 hrs. The accuracy of using the predicted CGM in place of the actual CGM output is assessed by the continuous glucose-error grid analysis (CG-EGA). Results demonstrate that a significant improvement in accuracy is achieved by using $CGM_{NE}w(t)$ in place of CGM(t). The root mean square error is reduced by 19% when an ad-hoc PH is tuned to each subject and by 14% when an "average" fixed PH is used for the entire population of patients. Finally, there is a significant improvement at hypoglycaemia: the number of data points falling in accurate or benign zones (A+B) of the CG-EGA increased by more than 20%.

Various objects and/or advantages of some preferred embodiments of the invention can be, in some preferred examples, achieved via the features of the independent claims attached hereto. Additional preferred embodiments are further set forth in the dependent claims.

BRIEF DESCRIPTION OF DRAWINGS

The invention can be best understood from the following detailed description of exemplary embodiments of the invention taken in conjunction with the accompanying drawings.

6

Figure 1:
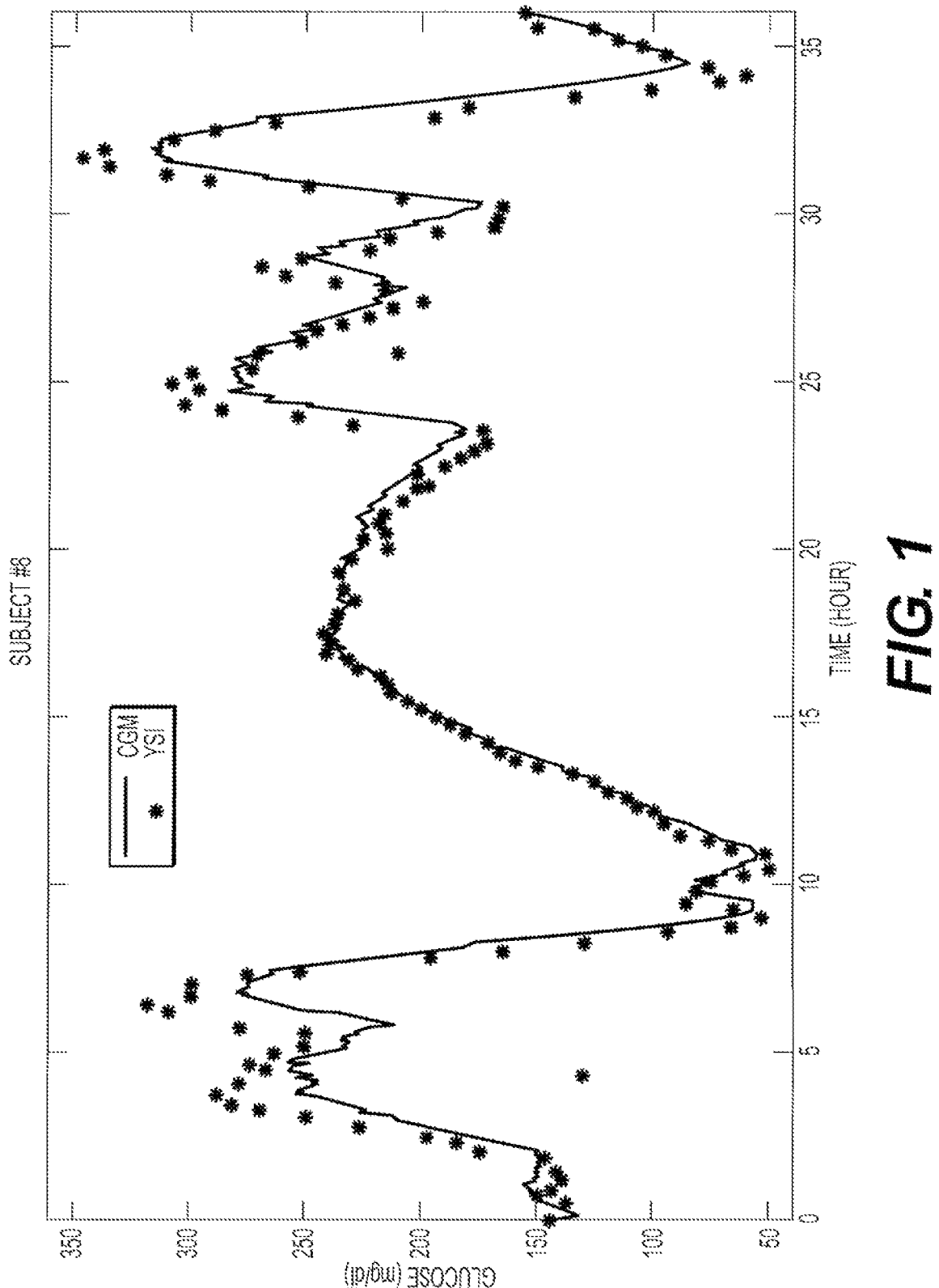
FIG. 1 shows a time graph of representative subject. BG references (stars) vs. CGM data (line) profiles.

FIG. 9 shows a table of combined P-EGA and R-EGA results for original CGM.

FIG. 10 shows a table of combined P-EGA and R-EGA results for original CGMNEW with PH=12.

FIG. 11 shows a table of combined P-EGA and R-EGA results for $CGM_{NE}w$ with individualized PH.

DETAILED DESCRIPTION

This invention provides a method, system, and device for improving accuracy of a continuous glucose monitoring through short-time prediction. For example, the accuracy of a continuous glucose sensor is improved.

In view of the many possible variations within the spirit of the invention, the invention will be discussed with reference to exemplary embodiments. However, it will be appreciated by those skilled in the art that the following discussion is for demonstration purposes, and should not be interpreted as a limitation of the invention. Other variations without departing from the spirit of the invention are applicable.

Mathematical Model
(Short-Time Prediction Algorithm)

In order to perform short-time prediction, an online denoising method recently presented [14] was further developed and implemented by using a Kalman filter (KF) coupled with a Bayesian smoothing criterion for the estimation of its unknown parameters.

In a stochastic context, let y(t) be the CGM value measured at time t:

$$y(t)=u(t)+v(t) \tag{1}$$

where u(t) is the true, unknown, glucose level and v(t) is random noise. The component v(t) is assumed to be additive, Gaussian, with zero mean and unknown variance equal to $\sigma^2$. It has been proven that a suitable and efficient model to represent u(t) is the double integration of white noise $$u(t)=2u(t-1)-u(t-2)+w(t) \tag{2}$$

where w(t) is a zero mean Gaussian noise with (unknown) variance equal to $\lambda^2$ [14]. The estimation of u(t) can be efficiently performed by using KF [22]. Converting Equations (1) and (2) into state-space form, and considering as state vector $x=[x-i(t)\ x2(t)]^T$, where $x_1(t)=u(t)$ and $x_2(t)=u(t-1)$, we obtain $$\begin{bmatrix} x_1(t+1) \\ x_2(t+1) \end{bmatrix} = \begin{bmatrix} 2 & -1 \\ 1 & 0 \end{bmatrix}\begin{bmatrix} x_1(t) \\ x_2(t) \end{bmatrix} + \begin{bmatrix} 1 \\ 0 \end{bmatrix}w(t) \tag{3a}$$

$$y(t) = [1 \ \ 0]\begin{bmatrix} x_1(t) \\ x_2(t) \end{bmatrix} + v(t) \tag{3b}$$

where Equations (3a) and (3b) are the process update and the measurement equations that are used by KF to estimate x(t|t), which is linear minimum-variance estimate of the state vector obtainable from the measurements y(t) collected until time t. For equations and details on the KF implementation we refer to [14, 21-23].

The only unknown parameters are the variance of the process and measurement noise, i.e. $\lambda^2$ and $\sigma^2$ values. However, $\lambda^2$ and $\sigma^2$ values could be efficiently estimated using the Bayesian smoothing criterion of [14]. Notably, in this way KF parameters reflect the specific signal-to-noise ratio (SNR) of the time series. This allows dealing with its variability between sensors and individuals and is a key advantage in denoising, which can be useful in prediction as well. For our purposes, we consider the prediction step of the KF $$x(t+1|t)=Fx(t|t) \qquad (4)$$

where F is the state-transition matrix (see Equation 3a), and x(t+1|t) is the state estimate based only on measurements collected until time t. Considering a suitable short-time prediction horizon (PH), one can re-iterate Equation (4) PH times, obtaining $$x(t+PH|t)=F^{PH}x(t|t) \qquad (5)$$

The left side, i.e. x̂(t+PH|t), is the predicted CGM value at time t+PH based on CGM data available until time t. If the chosen PH is close to the diffusion constant of the BG-to-IG kinetics (typically estimated at about 12 minutes [24] for the specific device used here), one may speculate that x̂(t+PH|t) can approximate the BG level at time t. The idea is thus to use short-time prediction and to substitute in real time the CGM output at time t, i.e. CGM(t), by a new value, which is $$CGM_{NEW}(t)=i_1(t+PH|t) \qquad (6)$$

Note: It is assumed that the CGM output is given every 1 minute. If the sampling period $T_s$ (in minutes) were different, the PH exponent in Equation (5) would become equal to PH divided by $T_s$, with the obvious constraint of having PH equal to $kT_s$, where k is an integer.

EXPERIMENTAL DATA

The dataset used to demonstrate the effectiveness of the proposed algorithm consists of 25 CGM traces for type I diabetic subjects, a subset of the database was previously reported in [25]. The CGM traces have been obtained using the Freestyle Navigator® (Abbott Diabetes Care, Alameda, CA), which operates with a sampling period of 1 minute. In addition, frequently measured BG references have been collected every 15 minutes with YSI BG analyzer (YSI, Inc., Yellow Springs, OH) for a period of at least 24 hours (see FIG. 1 for a representative data set).

Figure 2:
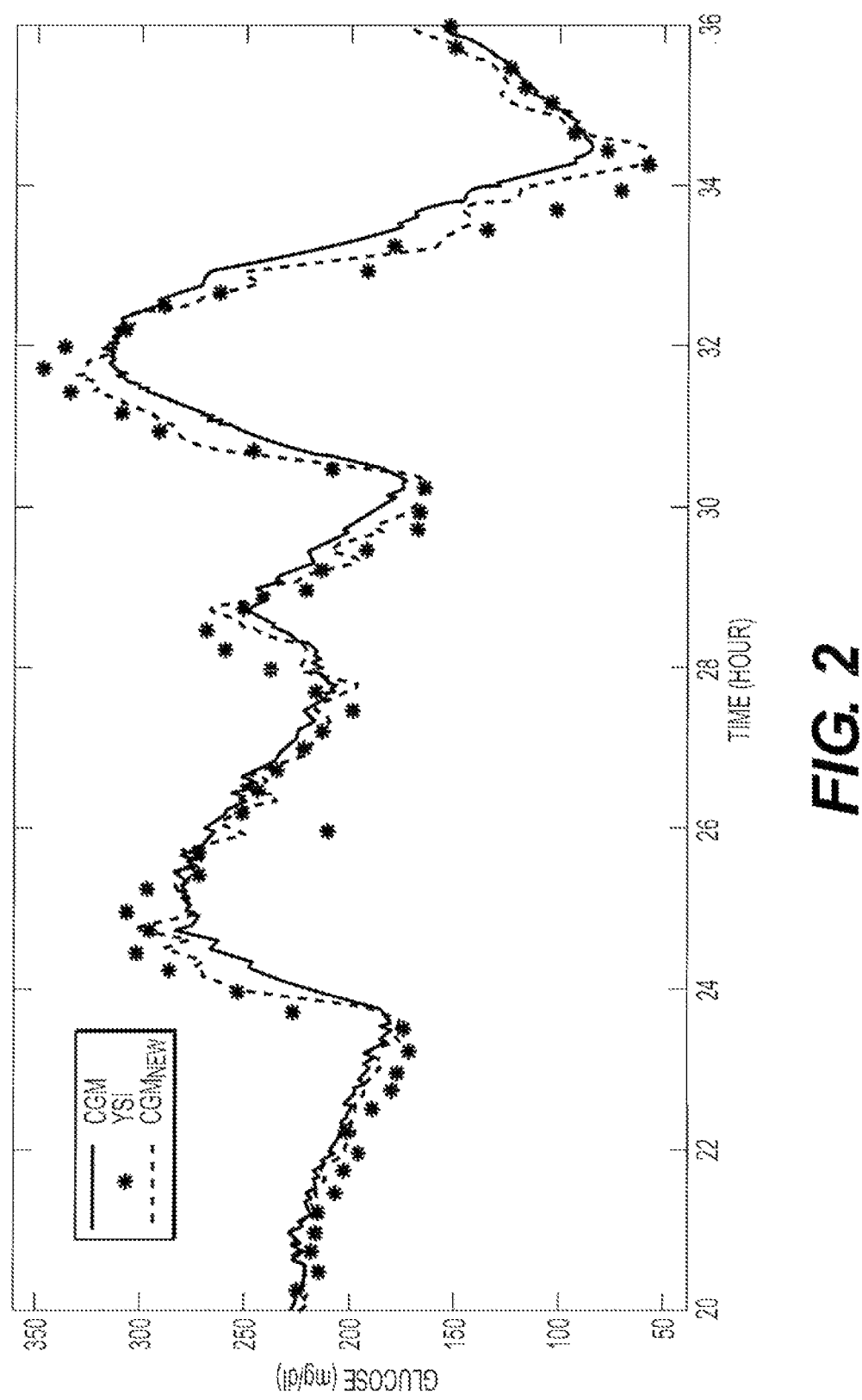
FIG. 2 shows a time graph of BG references (stars), CGM (line) and $CGM_{NE}w$ data (line) profiles.

As in [14], the estimation of $^2$ and $^2$ values has been performed in the first 6-hour portion of CGM data using the same stochastically-based smoothing criterion. However, because in this way prediction cannot be performed until 6 hours of data have been collected, it was decided to use an average value for the regularization parameter=$^2/^2$ (for instance, set to 0.001) to perform prediction in the 0-6 hours time window. The short-time prediction algorithm has been applied to each dataset simulating real-time working conditions. FIG. 2 shows the results of the application on the algorithm to the same representative subject of FIG. 1 (a section of the time window 20-36 hours is enlarged). The line is the original CGM profile, the stars are the BG references, and the line is the $CGM_{NEW}$ time series, obtained by applying to the short-time prediction algorithm with PH of 12 minutes (this value is taken from [24] and is the average estimated delay for the Freestyle Navigator®). As evident by inspecting the graph, the output of the prediction algorithm ($CGM_{NEW}$) appears able to compensate for part of the difference introduced by the BG-to-IG kinetics. The $CGM_{NEW}$ profile overlaps the YSI measurements better than the original, improving the accuracy of the sensor, especially close to peaks (e.g. around hour 32) and nadirs (e.g. around hour 34). Quantitatively, the root mean square error (RMSE) calculated between BG references and CGM data decreases from 27 mg/dL to 20 mg/dL, an improvement of about 27%.

Figure 3:
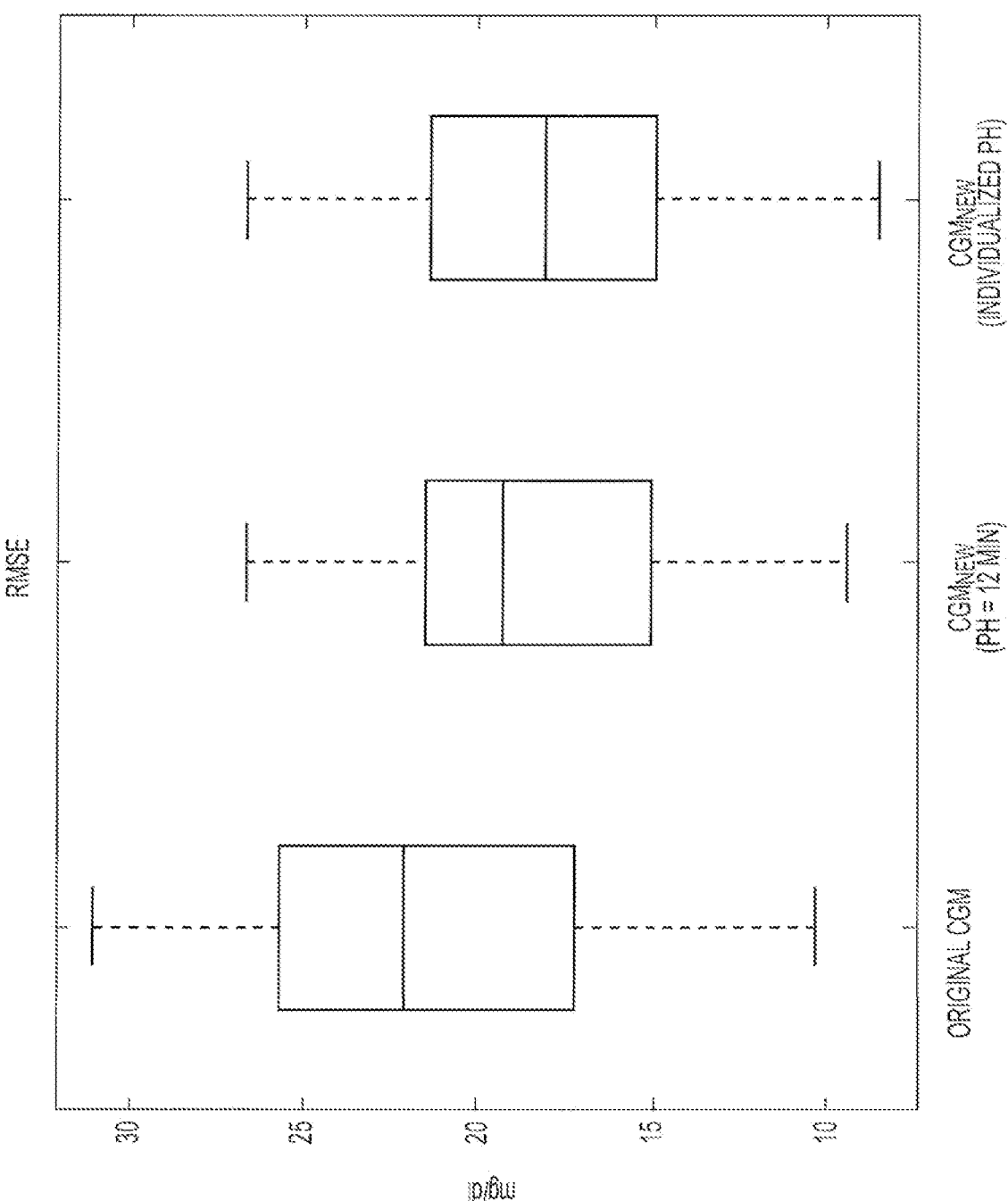
FIG. 3 shows boxplots of RMSE between BG references and CGM data. Left: original CGM. Middle: $CGM_{NE}w$ with PH=12 minutes. Right: CGMNEW with individualized PH. The line is the median value, the extremes of the box are the $25^{th}$ and $75^{th}$ percentiles, and the whiskers extend to the most extreme data points.

Quantitative results of the application of the algorithm to all 25 datasets are graphically illustrated and summarized in the boxplots of FIG. 3. The boxplot on the left is a compact representation of RMSE values calculated between BG references and original CGM data, while the middle boxplot presents RMSE values calculated between BG and $CGM_{NEW}$ data (PH=12). For each boxplot, the line is the median RMSE value, the extremes of the box are the $25^{th}$ and $75^{th}$ percentiles, and the whiskers extend to the most extreme data points. Comparing the two boxplots, the enhancement in the accuracy of CGM output is evident: the RMSE decreases significantly for all subjects (p=0.05). In particular, the median RMSE decreases from 22.1 to 19.2 mg/dL (a relative improvement of about 14%).

Figure 4:
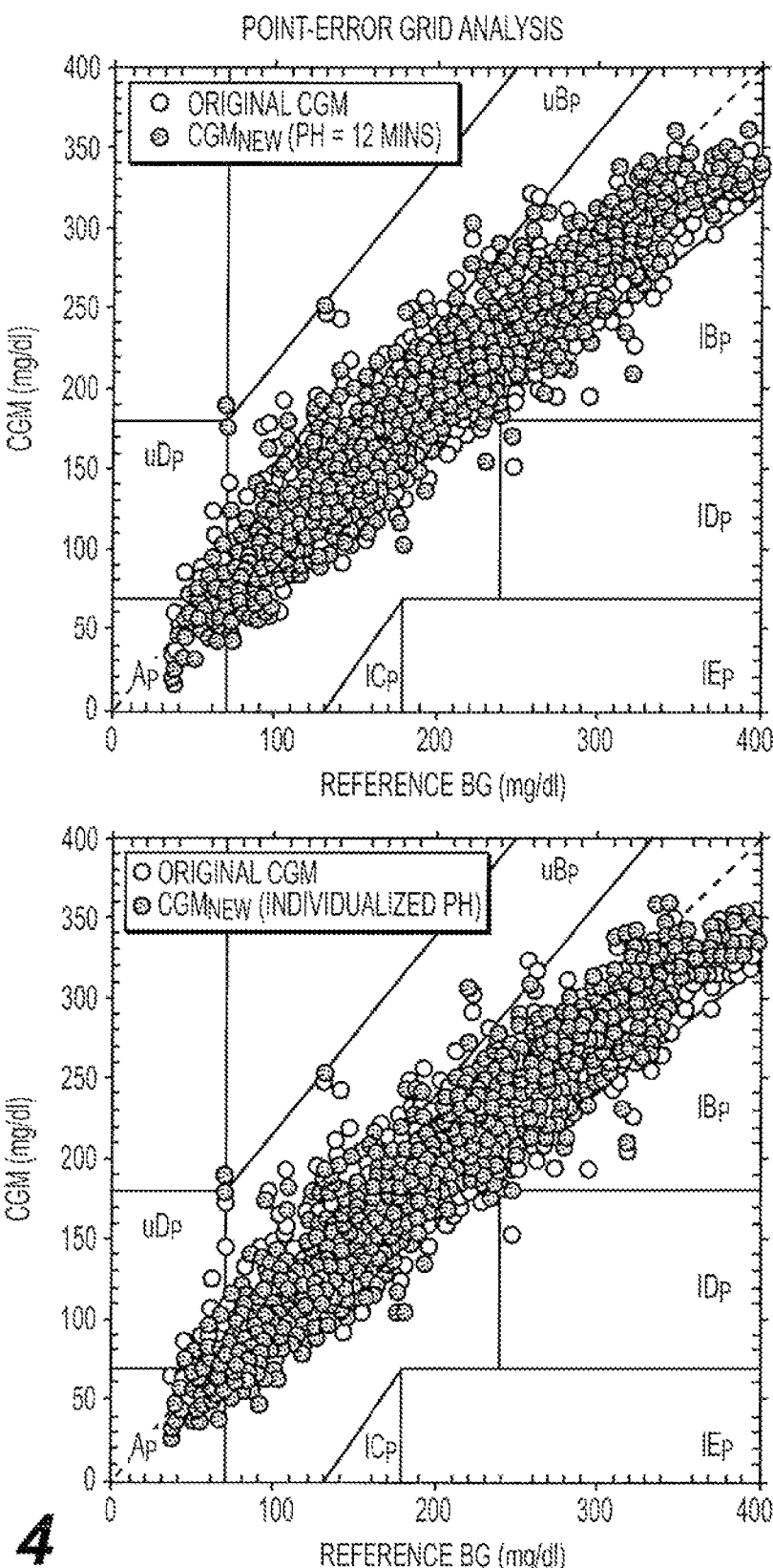
FIG. 4 shows P-EGA (left) and R-EGA (right) comparing results obtained from original CGM data (circles) with $CGM_{NE}w$ with PH=12 minutes (top, circles) and $CGM_{NEW}$ with individualized PH (bottom, circles).
Figure 4:
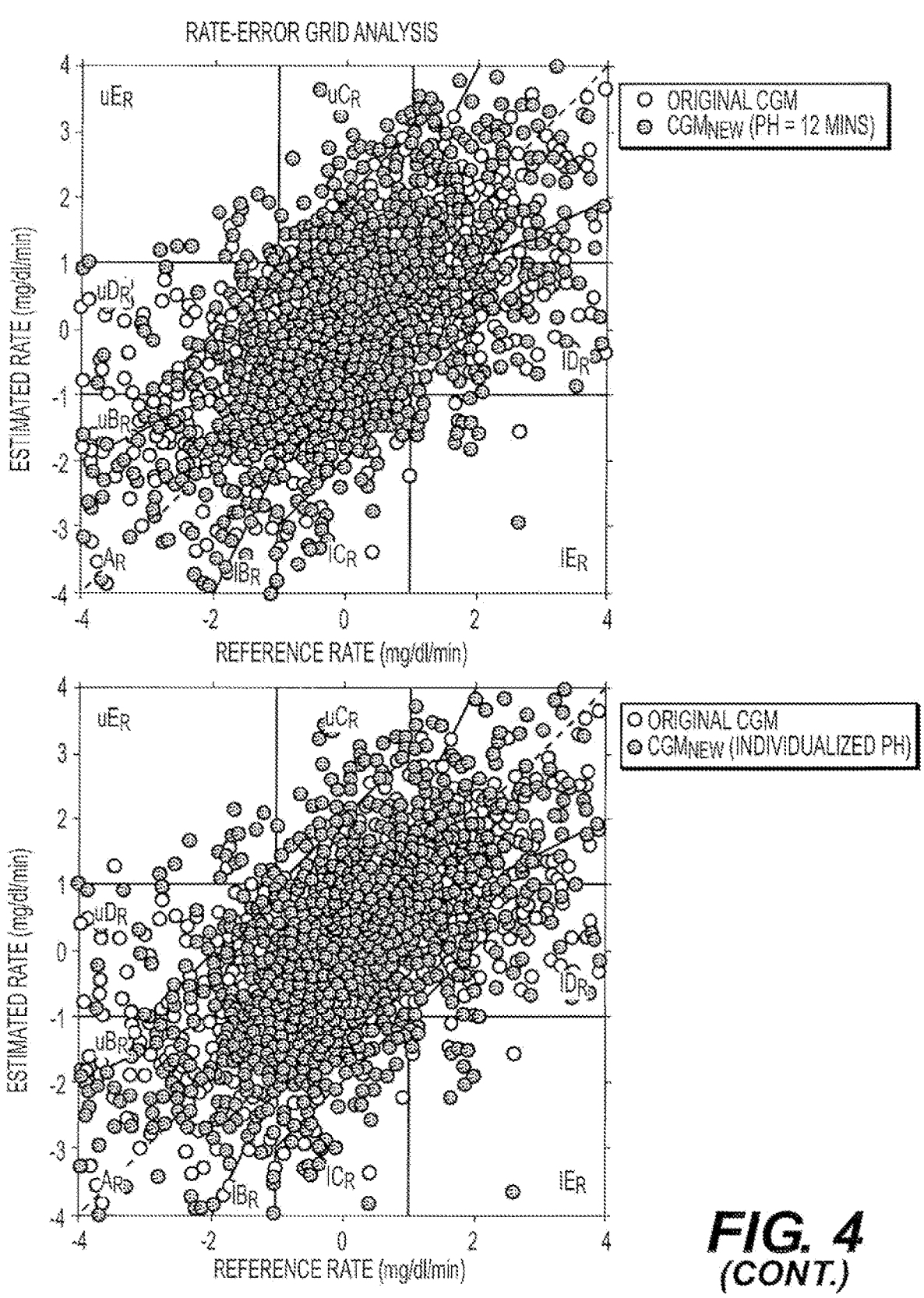

The second index used to quantify the improvement introduced by using short-time prediction algorithm is the continuous glucose-error grid analysis (CG-EGA) [25]. The CG-EGA is one of the methods widely used for assessing the clinical accuracy of CGM data, and for reporting accuracy in each of three relevant glycemic ranges, hypoglycemia, euglycemia, and hyperglycemia. FIG. 4 shows P-EGA (left) and R-EGA (right) obtained by using the $CGM_{NEW}$ data with PH=12 (top, circles) and original CGM data (top, circles). A total of 2630 data pairs are included. The graphics imply that the number of data pairs in the dangerous (D) zone significantly decreases (from 36.7% to 23.3%), thus confirming the results of FIG. 2. This is also supported by the numerical results shown in FIG. 9, which presents the CG-EGA matrix [25] results when using original CGM data. The percentage of clinically accurate readings and readings resulting in benign errors (i.e. A+B zone) is 63.3% at hypoglycemia, 99.4% at euglycemia, and 99.7% in hyperglycemia. FIG. 10 shows the results obtained by $CGM_{NEW}$ with PH=12 minutes. Compared with values shown in FIG. 9, the percentage of data pairs falling in A+B zone increases significantly to 76.7% at hypoglycemia (relative improvement of about 21%), while the values for euglycemia and hyperglycemia remain unchanged.

Because of the variability from individual to individual of the diffusion constant of BG-to-IG kinetics [12,26], one can argue that the choice of a fixed PH could not be optimal. For this reason, we also performed a second analysis, individualizing the PH value to understand W the performance of the algorithm could be further improved. For each subject, PH values from 1 to 30 minutes have been tested, and the PH value which returned the lowest RMSE has been retrospectively selected as optimal. Results of this retrospective analysis show that the individualized PH value varies from subject to subject, from a minimum of 5 minutes to a maximum of 22 minutes, confirming the results obtained in [12,26] The boxplot summarizing RMSE results of the application of the short-time prediction algorithm with individualized PH is on the right side of FIG. 3. Comparing left (original CGM) and right boxplots, the RMSE decreases significantly for all subjects (p=0.04), with the median RMSE decreasing from 22.1 to 18.0 mg/dL (a relative improvement of about 19%). However, comparing results of middle ($CGM_{NEW}$ with PH=12) and right boxplots, no significant differences have been achieved. This result is also confirmed by the CG-EGA, graphically depicted in the panels of the bottom row of FIG. 4. Note that, even W the number of data pairs falling in the D zone decreases from 37.7% to 21.8%, this results is not substantially different from the one obtained with PH=12 (23.3%). Finally, analyzing the results shown in FIG. 11, the percentage of data pairs falling in A+B zone is also very similar to the results obtained using a fixed PH. This evidences that the choice of individualizing the PH value does not result in significant improvement in the performance of the prediction algorithm.

Figure 5:
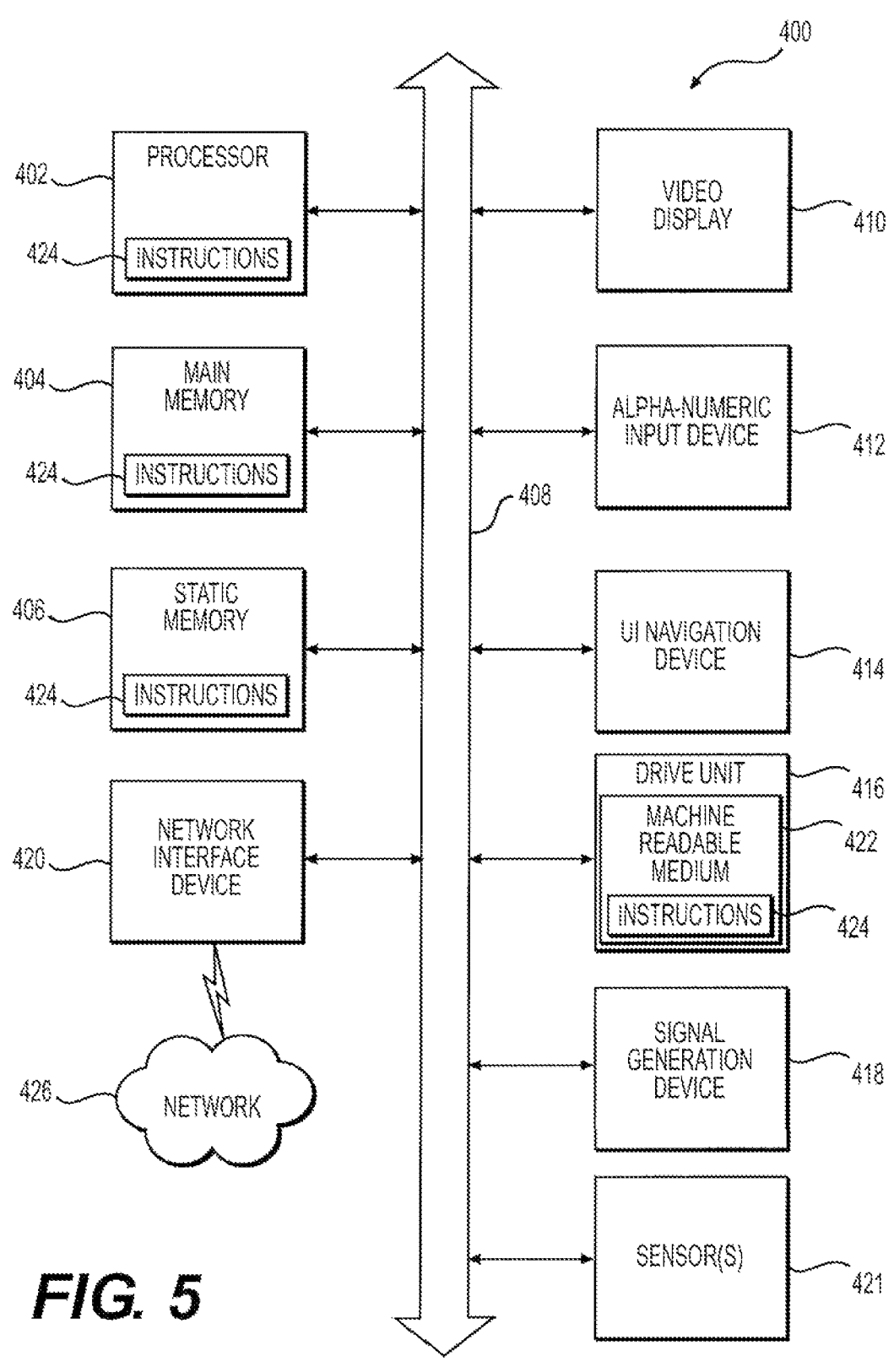
FIG. 5 shows a block diagram illustrating an example of a machine upon which one or more aspects of embodiments of the present invention can be implemented.

FIG. 5 is a block diagram illustrating an example of a machine upon which one or more aspects of embodiments of the present invention can be implemented.

FIG. 5 illustrates a block diagram of an example machine 400 upon which one or more embodiments (e.g., discussed methodologies) can be implemented (e.g., run).

Examples of machine 400 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or more processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module (e.g. denoising module), subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 400) and software architectures that can be deployed in example embodiments.

In an example, the machine 400 can operate as a standalone device or the machine 400 can be connected (e.g., networked) to other machines. In a networked deployment, the machine 400 can operate in the capacity of either a server or a client machine in server-client network environments. In an example, machine 400 can act as a peer machine in peer-to-peer (or other distributed) network environments. The machine 400 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 400. Further, while only a single machine 400 is illustrated, the term "machine" shall also be taken to include any collection of machines that individually or jointly execute a set (or multiple sets) of instructions to perform any one or more of the methodologies discussed herein.

Example machine (e.g., computer system) 400 can include a processor 402 (e.g., a central processing unit (CPU), a graphics processing unit (GPU) or both), a main memory 404 and a static memory 406, some or all of which can communicate with each other via a bus 408. The machine 400 can further include a display unit 410, an alphanumeric input device 412 (e.g., a keyboard), and a user interface (UI) navigation device 411 (e.g., a mouse). In an example, the display unit 810, input device 417 and UI navigation device 414 can be a touch screen display. The machine 400 can additionally include a storage device (e.g., drive unit) 416, a signal generation device 418 (e.g., a speaker), a network interface device 420, and one or more sensors 421, such as a global positioning system (GPS) sensor, compass, accelerometer, or other sensor.

The storage device 416 can include a machine readable medium 422 on which is stored one or more sets of data structures or instructions 424 (e.g., software) embodying or utilized by any one or more of the methodologies or functions described herein. The instructions 424 can also reside, completely or at least partially, within the main memory 404, within static memory 406, or within the processor 402 during execution thereof by the machine 400. In an example, one or any combination of the processor 402, the main memory 404, the static memory 406, or the storage device 416 can constitute machine readable media.

While the machine readable medium 422 is illustrated as a single medium, the term "machine readable medium" can include a single medium or multiple media (e.g., a centralized or distributed database, and/or associated caches and servers) that configured to store the one or more instructions 424. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 424 can further be transmitted or received over a communications network 426 using a transmission medium via the network interface device 420 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

The machine 400 can be configured or arranged to include a denoising module (e.g. software and/or hardware, circuit(s)) for generating an improved accuracy CGM from the signal received from the continuous glucose sensor (CGS) by reducing random noise and calibration errors using real-time short-time glucose prediction.

Figure 6:
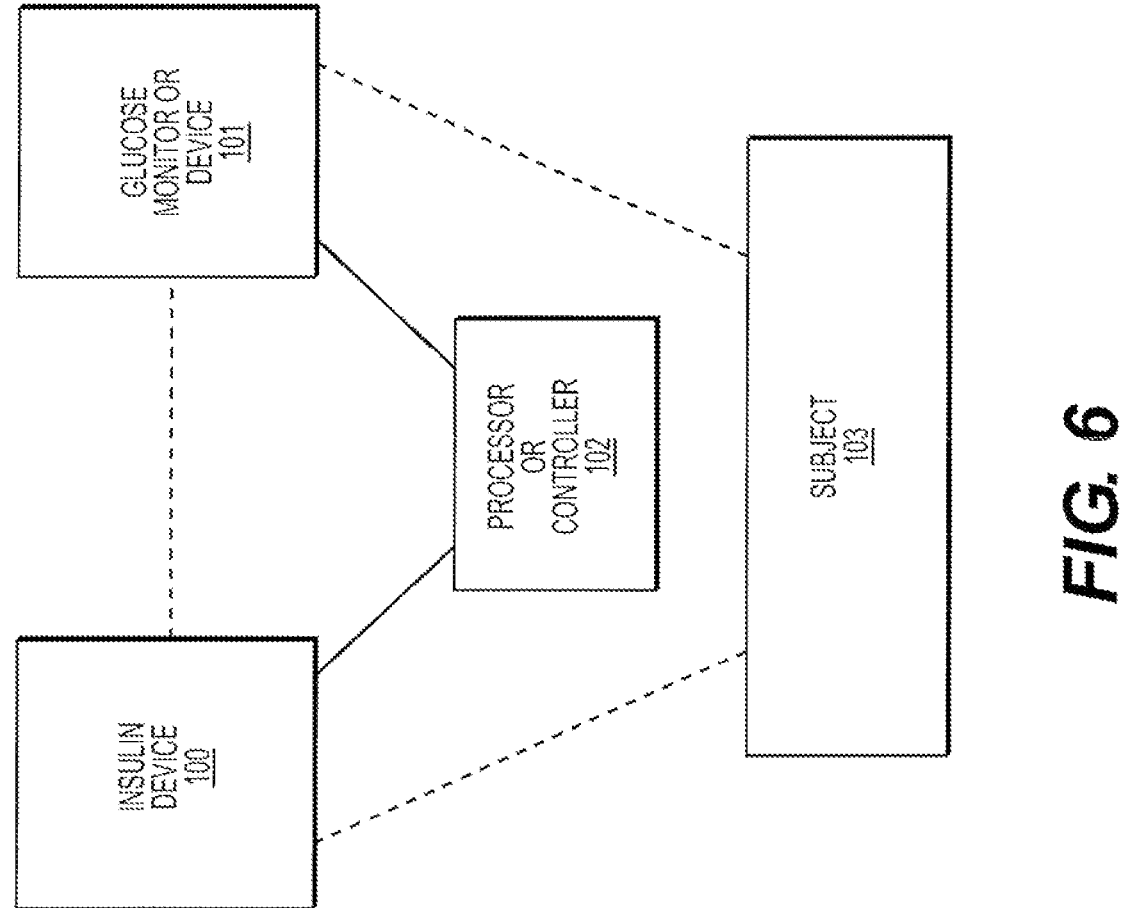
FIG. 6 shows a high level functional block diagram of an embodiment of the invention.

FIG. 6 is a high level functional block diagram of an embodiment of the invention.

As shown in FIG. 6, a processor or controller 102 may communicate with the glucose monitor or device 101, and optionally the insulin device 100. The glucose monitor or device 101 may communicate with the subject 103 to monitor glucose levels of the subject 103. The processor or controller 102 is configured to perform the required calculations. Optionally, the insulin device 100 may communicate with the subject 103 to deliver insulin to the subject 103. The processor or controller 102 is configured to perform the required calculations. The glucose monitor 101 and the insulin device 100 may be implemented as a separate device or as a single device. The processor 102 can be implemented locally in the glucose monitor 101, the insulin device 100, or a standalone device (or in any combination of two or more of the glucose monitor, insulin device, or a stand along device). The processor 102 or a portion of the system can be located remotely such that the device is operated as a telemedicine device.

Figure 7A:
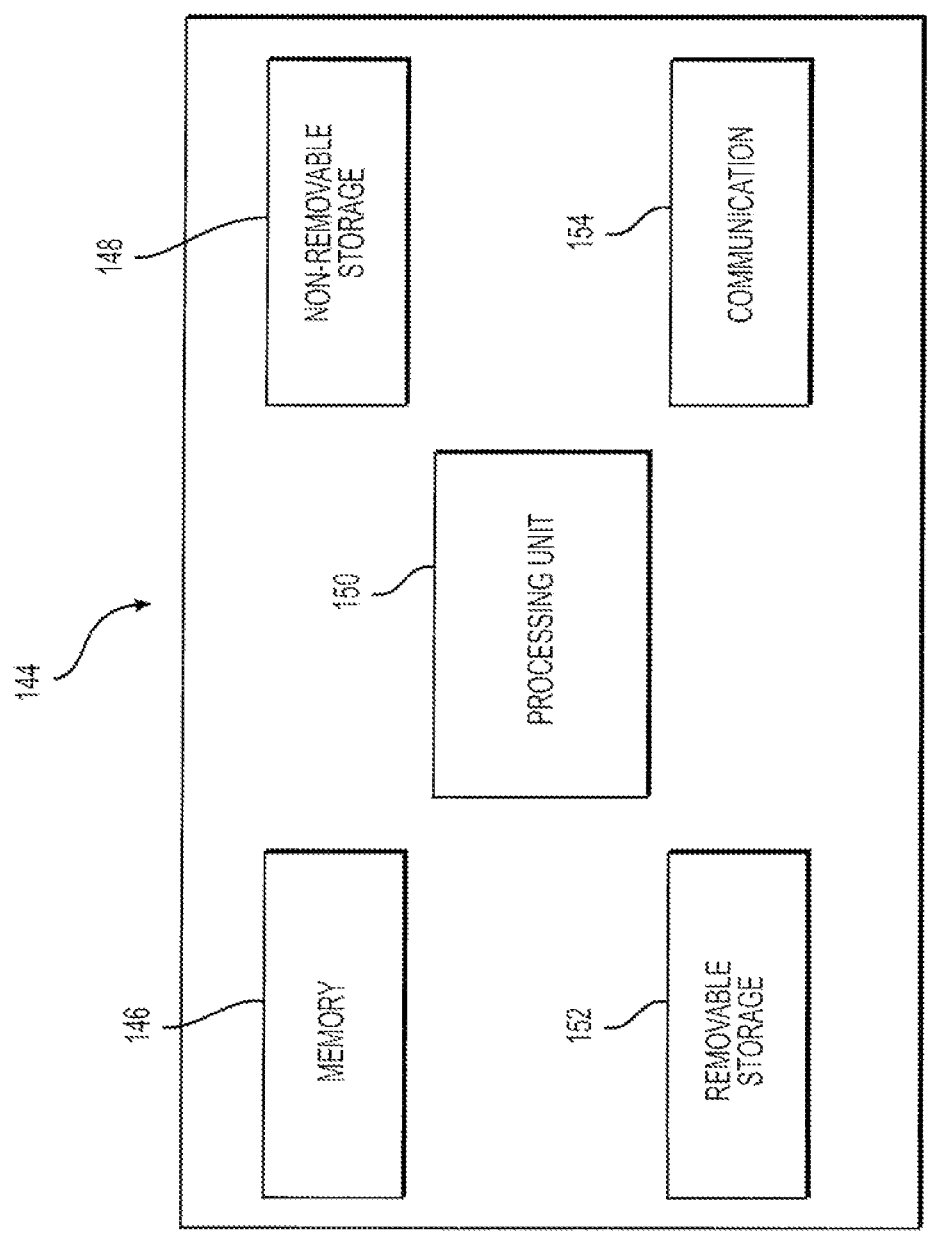
FIG. 7A shows a block diagram of a most basic configuration of a computing device.

Referring to FIG. 7A, in its most basic configuration, computing device 144 typically includes at least one processing unit 150 and memory 146. Depending on the exact configuration and type of computing device, memory 146 can be volatile (such as RAM), non-volatile (such as ROM, flash memory, etc.) or some combination of the two.

Additionally, device 144 may also have other features and/or functionality. For example, the device could also include additional removable and/or non-removable storage including, but not limited to, magnetic or optical disks or tape, as well as writable electrical storage media. Such additional storage is provided by removable storage 152 and non-removable storage 148. Computer storage media includes volatile and nonvolatile, removable and non-removable media implemented in any method or technology for storage of information such as computer readable instructions, data structures, program modules (e.g. denoising module) or other data. The memory, the removable storage and the non-removable storage are all examples of computer storage media. Computer storage media includes, but is not limited to, RAM, ROM, EEPROM, flash memory or other memory technology CDROM, digital versatile disks (DVD) or other optical storage, magnetic cassettes, magnetic tape, magnetic disk storage or other magnetic storage devices, or any other medium which can be used to store the desired information and which can accessed by the device. Any such computer storage media may be part of, or used in conjunction with, the device. The device may also contain one or more communications connections 154 that allow the device to communicate with other devices (e.g. other computing devices). The communications connections carry information in a communication media. Communication media typically embodies computer readable instructions, data structures, program modules (e.g. denoising module) or other data in a modulated data signal such as a carrier wave or other transport mechanism and includes any information delivery media. The term "modulated data signal" means a signal that has one or more of its characteristics set or changed in such a manner as to encode, execute, or process information in the signal. By way of example, and not limitation, communication medium includes wired media such as a wired network or direct-wired connection, and wireless media such as radio, RF, infrared and other wireless media. As discussed above, the term computer readable media as used herein includes both storage media and communication media.

Figure 7B:
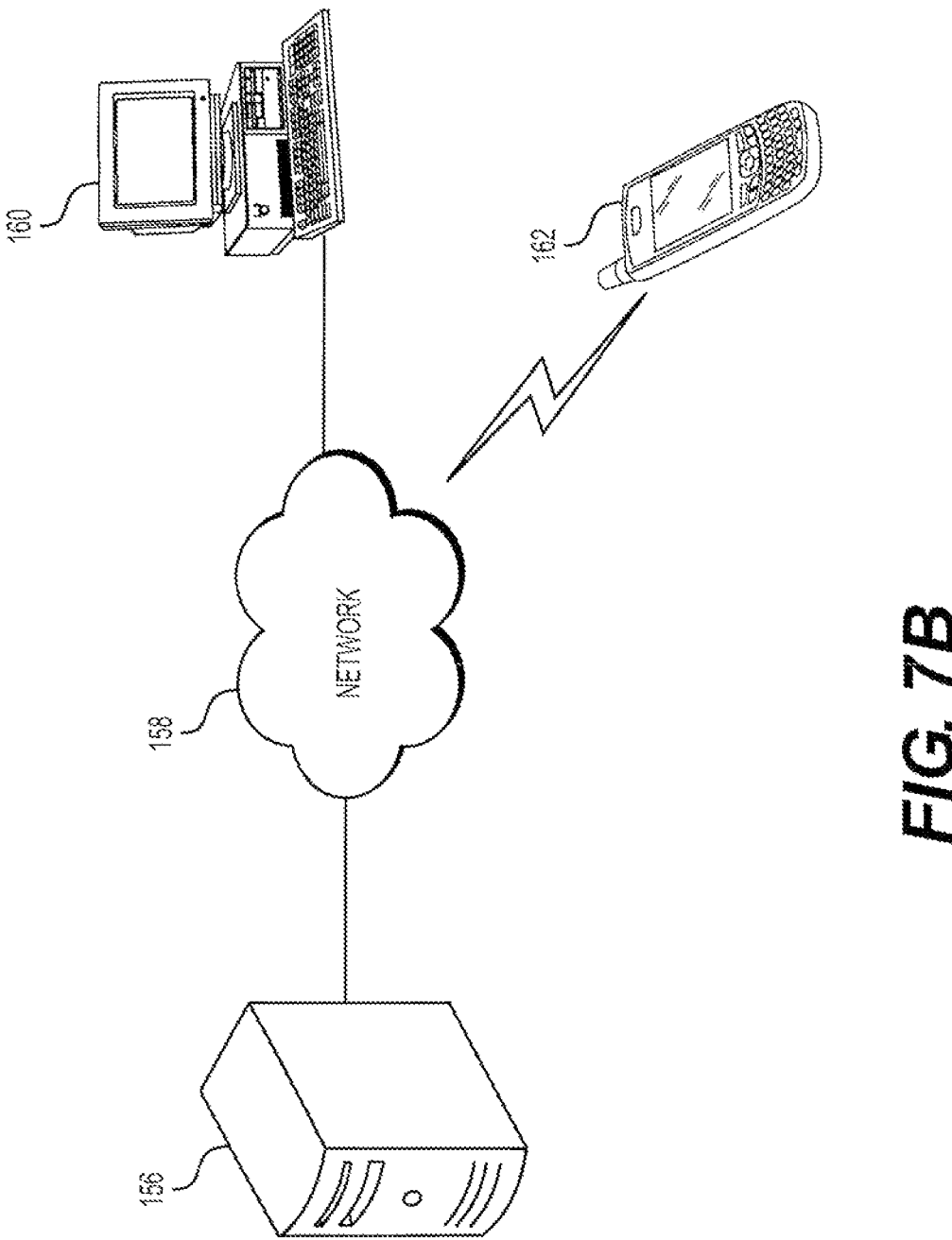
FIG. 7B shows a network system in which embodiments of the invention can be implemented.

In addition to a stand-alone computing machine, embodiments of the invention can also be implemented on a network system comprising a plurality of computing devices that are in communication with a networking means, such as a network with an infrastructure or an ad hoc network. The network connection can be wired connections or wireless connections. As a way of example, FIG. 7B illustrates a network system in which embodiments of the invention can be implemented. In this example, the network system comprises computer 156 (e.g. a network server), network connection means 158 (e.g. wired and/or wireless connections), computer terminal 160, and PDA (e.g. a smart-phone) 162 (or other handheld or portable device, such as a cell phone, laptop computer, tablet computer, GPS receiver, mp3 player, handheld video player, pocket projector, etc. or handheld devices (or non portable devices) with combinations of such features). In an embodiment, it should be appreciated that the module listed as 156 may be glucose monitor device. In an embodiment, it should be appreciated that the module listed as 156 may be a glucose monitor device and an insulin device. Any of the components shown or discussed with FIG. 7B may be multiple in number. The embodiments of the invention can be implemented in anyone of the devices of the system. For example, execution of the instructions or other desired processing can be performed on the same computing device that is anyone of 156, 160, and 162. Alternatively, an embodiment of the invention can be performed on different computing devices of the network system. For example, certain desired or required processing or execution can be performed on one of the computing devices of the network (e.g. server 156 and/or glucose monitor device), whereas other processing and execution of the instruction can be performed at another computing device (e.g. terminal 160) of the network system, or vice versa. In fact, certain processing or execution can be performed at one computing device (e.g. server 156 and/or glucose monitor device); and the other processing or execution of the instructions can be performed at different computing devices that may or may not be networked. For example, the certain processing can be performed at terminal 160, while the other processing or instructions are passed to device 162 where the instructions are executed. This scenario may be of particular value especially when the PDA 162 device, for example, accesses to the network through computer terminal 160 (or an access point in an ad hoc network). For another example, software to be protected can be executed, encoded or processed with one or more embodiments of the invention. The processed, encoded or executed software can then be distributed to customers. The distribution can be in a form of storage media (e.g. disk) or electronic copy.

For example, a denoising module for generating an improved accuracy CGM signal by reducing random noise and calibration errors using real-time short-time glucose prediction can be software and/or hardware configured and/or arranged as described above.

Figure 8:
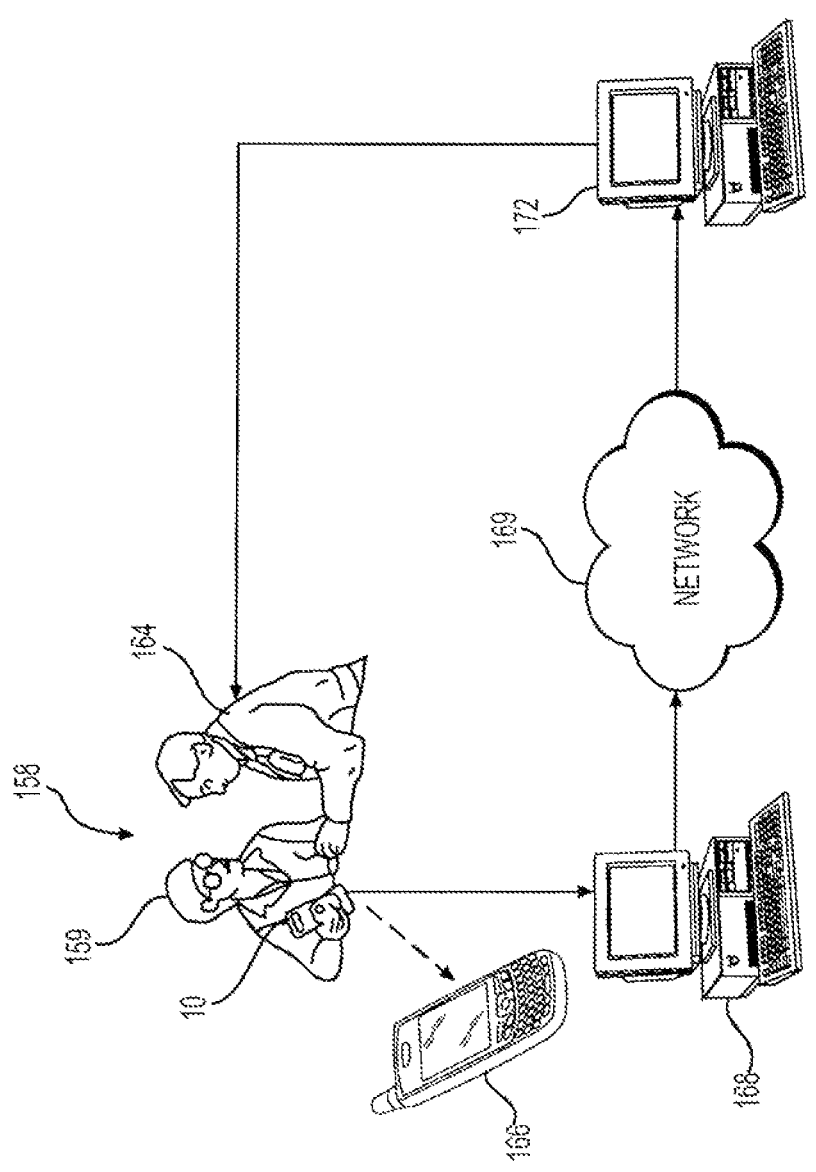
FIG. 8 shows a system in which one or more embodiments of the invention can be implemented using a network, or portions of a network or computers.

FIG. 8 illustrates a system in which one or more embodiments of the invention can be implemented using a network, or portions of a network or computers.

FIG. 8 diagrammatically illustrates an exemplary system in which examples of the invention can be implemented. In an embodiment the glucose monitor may be implemented by the subject (or patient) at home or other desired location. However, in an alternative embodiment it may be implemented in a clinic setting or assistance setting. For instance, referring to FIG. 8, a clinic setup 158 provides a place for doctors (e.g. 164) or clinician/assistant to diagnose patients (e.g. 159) with diseases related with glucose. A glucose monitoring device 10 can be used to monitor and/or test the glucose levels of the patient. It should be appreciated that while only glucose monitor device 10 is shown in the system of the invention and any component thereof may be used in the manner depicted by FIG. 8. The system or component may be affixed to the patient or in communication with the patient as desired or required. For example the system or combination of components thereof—including a glucose monitor device 10, a controller 12, or an insulin pump 14, or any other device or component—may be in contact or affixed to the patient through tape or tubing or may be in communication through wired or wireless connections. Such monitor and/or test can be short term (e.g. clinical visit) or long term (e.g. clinical stay or family). The glucose monitoring device outputs can be used by the doctor (clinician or assistant) for appropriate actions, such as insulin injection or food feeding for the patient, or other appropriate actions. Alternatively, the glucose monitoring device output can be delivered to computer terminal 168 for instant or future analyses. The delivery can be through cable or wireless or any other suitable medium. The glucose monitoring device output from the patient can also be delivered to a portable device, such as PDA 166. The glucose monitoring device outputs with improved accuracy can be delivered to a glucose monitoring center 172 for processing and/or analyzing. Such delivery can be accomplished in many ways, such as network connection 170, which can be wired or wireless.

In addition to the glucose monitoring device outputs, errors, parameters for accuracy improvements, and any accuracy related information can be delivered, such as to computer 168, and/or glucose monitoring center 172 for performing error analyses. This can provide a centralized accuracy monitoring and/or accuracy enhancement for glucose centers, due to the importance of the glucose sensors.

Examples of the invention can also be implemented in a standalone computing device associated with the target glucose monitoring device. An exemplary computing device in which examples of the invention can be implemented is schematically illustrated in FIG. 7A.

In summary, having accurate readings from a continuous glucose monitoring (CGM) device is essential to make CGM systems even more reliable in a daily-life application perspective, in particular because the more the accuracy of CGM device the better the real-time detection of hypoglycemic and hyperglycemic events. Nowadays, the accuracy of CGM devices is still suboptimal because problems related to calibration errors and the presence of the BG-to-IG kinetic system which also affects the calibration process.

The short-time prediction, i.e. with prediction horizon PH less than 20 minutes, should be considered as an effective solution to improve the accuracy of CGM devices since it compensates part of the delay due to the BG-to-IG kinetic system.

This aspect can be potentially of commercial interest for CGM manufacturers because the suboptimal accuracy of CGM sensors is one of the factors that do not allow CGM to be accepted by FDA as substitute of self monitoring finger-sticks.

Another important feature obtained as a by-product by an aspect of an embodiment of the present invention is the real-time prediction of the future glucose concentration. The possibility of generating also a preventive alert before the event occurs can have a potential impact for CGM manufacturers, because it can make any alert generation system timelier in alarming the patient for hypo/hyperglycemic events.

U.S. Pat. No. 7,806,886 by Medtronic provides a filter that presents several limitations. First, it needs to be identified on specific data, second its structure needs to be modified if applied to CGM devices other than the ones of Medtronic (because the sampling period may change), third, because the "raw deconvolution" is exposed to ill-conditioning (see De Nicolao et al. [27]).

The PCT publication No. 2007027691A/-1 (PCT Application No. PCT/US2006/033724), entitled "Improving the accuracy of continuous glucose sensors" provides the BG reconstruction that is performed by a numerical approximation, which may in limited instances be exposed to ill-conditioning of inverse problems.

An aspect of an embodiment of the present invention method, system, and computer readable medium provides, but not limited thereto, an innovation that lies in using a short-time prediction to improve accuracy of CGM readings by compensating part of the delay with BG measurements due to the BG-to-IG kinetics. The implementation of short-time prediction here proposed is optimal with respect to other implementations, because is able to take into account possible SNR variations of CGM data during the monitoring, thanks to an automatic stochastically-based Bayesian estimation procedure of the unknown parameters of the algorithm.

Both methods of the U.S. Pat. No. 7,806,886 patent and the 2007027691A/-1 application are very different from the solution proposed in the present invention, because but not limited thereto, none of those methods exploits short-time prediction to compensate the delay due to the presence of the BG-to-IG kinetics.

An aspect of various embodiments of the present invention may provide a number of advantages, such as but not limited thereto, a short-time prediction that is an effective solution to improve CGM accuracy and compensating part of the delay with BG measurements due to the BG-to-IG kinetics. First, it does not contain any physiological model to be identified. Second, it does not need to be modified if the CGM device changes. Third, the proposed implementation circumvents ill-conditioning of inverse problems.

An aspect of various embodiments of the present invention may be utilized for a number of products and services, such as but not limited thereto, a commercial impact on CGM devices. In fact, in the preliminary study that the present inventors performed, we showed that it allows improving the accuracy of the output of CGM sensors by more than 15%. As said above, this can be of interest for CGM manufacturers because the suboptimal accuracy of CGM sensors is one of the factors that do not allow CGM to be accepted as substitute of finger-stick measures. In addition, the more accurate CGM readings, the better the hypoglycemia and hyperglycemia detection.

Finally, the improvement of the accuracy of CGM data of various embodiments of the present invention can be important also for real-time applications based on CGM data, e.g. for the improvement of the accuracy of the CGM signal, which is a key element in closed-loop algorithms for artificial pancreas experiments.

APPENDIX A

The following patents, applications and publications as listed below and throughout this document are hereby incorporated by reference in their entirety herein (and which are not admitted to be prior art with respect to the present invention by inclusion in this section).

1. Garg K, Zisser H, Schwartz S, Bailey T, Kaplan R, Ellis S, Jovanovic L. Improvement in glycemic excursions with a transcutaneous, real-time continuous glucose sensor. Diabetes Care. 2008; 29{1}:44-50.
2. Klonoff D C. Continuous glucose monitoring: Roadmap for 21st century diabetes therapy. Diabetes Care. 2005; 28(5):1231-9.
3. Deiss D, Bolinder J, Riveline J, Battelino T, Bosi E, Tubiana-Rufi N, Kerr D, Phillip M. Improved glycemic control in poorly controlled patients with type 1 diabetes using real-time continuous glucose monitoring. Diabetes Care. 2006; 29{12}:2730-2.
4. Juvenile Diabetes Research Foundation Continuous Glucose Monitoring Study Group, Tamborlane V V V, Beck R W, Bode B W, Buckingham B, Chase H P, Clemons R, Fiallo-Scharer R, Fox L A, Gilliam L K, Hirsch I B, Huang E S, Kollman C, Kowalski A J, Laffel L, Lawrence J M, Lee J, Mauras N, O'Grady M, Ruedy K J, Tansey M, Tsalikian E, Weinzimer S, Wilson D M, Woipert H, Wysocki T, Xing D. Continuous glucose monitoring and intensive treatment of type 1 diabetes. N Eng! J Med. 2008; 359(14):1484-76.
5. Bequette B W. A critical assessment of algorithms and challenges in the development of a closed-loop artificial pancreas. Diabetes Technol Ther. 2005; 7(1):28-47.
6. Cobelli C, Dalla Man C, Sparacino G, Magni L, De Nicolao G, Kovatchev B P. Diabetes: Models, Signals, and Control. IEEE rev biomed Eng. 2010; 2(2):54-96.
7. Bruttomesso D, Farret A, Costa S, Marescotti M C, Vettore M, Avogaro A, Tiengo A, Dalla Man C, Place J, Facchinetti A, Guerra S, Magni L, De Nicolao G, Cobelli C, Renard E, Maran A. Closed-Loop Artificial Pancreas Using Subcutaneous Glucose Sensing and Insulin Delivery and a Model Predictive Control Algorithm: Preliminary Studies in Padova and Montpellier. J Diabetes Sci Technol. 2009; 3(5):1014-21.

8. www.diadvisor.eu [accessed on Mar. 29, 2010].

9. Kovatchev B, Anderson S, Heinemann L, Clarke W. Comparison of the numerical and clinical accuracy of four continuous glucose monitors. Diabetes Care. 2008; 31 (6):1160-4.

10. Clarke W L, Anderson S, Kovatchev B. Evaluating clinical accuracy of continuous glucose monitoring systems: Continuous Glucose-Error Grid Analysis (CG-EGA). Curr Diabetes Rev. 2008; 4(3):193-9. Review.

11. Rebrin K, Steil G M, van Antwerp W P, Subcutaneous glucose predicts plasma glucose independent of insulin: implications for continuous monitoring. Am J Physiol. 1999; 277(3 Pt 1):E561-71.

12. Keenan D B, Mastrototaro J J, Voskanyan G, Steil G M. Delays in Minimally Invasive Continuous Glucose Monitoring Devices: A Review of Current Technology. J Diabetes Sci Technol. 2009; 3(5):1207-14.

13. Facchinetti A, Sparacino G, Cobelli C. Modeling the Error of Continuous Glucose Monitoring Sensor Data: Critical Aspects Discussed through Simulation Studies. J Diabetes Sci Technol. 2010; 4(1):4-14.

14. Facchinetti A, Sparacino G, Cobelli C. An online self-tunable method to denoise CGM sensor data. IEEE Trans Biomed Eng. 2010; 57(3):634-41.

15. Diabetes Research In Children Network (Direcnet) Study Group, Buckingham B A, Kollnnan C, Beck R, Kalajian A, Fiallo-Scharer R, Tansey M J, Fox L A, Wilson D M, Weinzimer S A, Ruedy K J, Tamborlane W V. Evaluation of factors affecting CGMS calibration. Diabetes Technol Ther. 2006; 8(3):318-25.

16. King C, Anderson S M, Breton M, Clarke W L, Kovatchev B P. Modeling of calibration effectiveness and blood-to-interstitial glucose dynamics as potential confounders of the accuracy of continuous glucose sensors during hyperinsulinemic clamp. J Diabetes Sci Technol. 2007; 1 (3):317-22.

17. Kuure-Kinsey M, Palerm C C, Bequette B W. A dual-rate Kalman filter for continuous glucose monitoring. Conf Proc IEEE Eng Med Biol Soc. 2006; 1:63-6.

18. Sparacino G, Zanderigo F, Corazza S, Maran A, Facchinetti A, Cobelli C. Glucose concentration can be predicted ahead in time from continuous glucose monitoring sensor time-series. IEEE Trans Biomed Eng. 2007; 54(5):931-7.

19. Gani A, Gribok A V, Rajaraman S, Ward W K, Reifman J. Predicting subcutaneous glucose concentration in humans: data-driven glucose modeling. IEEE Trans Biomed Eng. 2009; 56(2):246-54.

20. Perez-Gandia C, Facchinetti A, Sparacino G, Cobelli C, Gomez E J, Rigla M, de Leiva A, Hernando M E. Artificial neural network algorithm for online glucose prediction from continuous glucose monitoring. Diabetes Technol Ther. 2010; 12(1):81-8.

21. Palerm C C, Willis J P, Desemone J, Bequette B W. Hypoglycemia prediction and detection using optimal estimation. Diabetes Technol Ther. 2005; 7(1):3-14.

22. Anderson B D O and Moore J B. Optimal Filtering. Dover Publications, 2005.

23. Bequette B W. Continuous glucose monitoring: real-time algorithms for calibration, filtering, and alarms. J Diabetes Sci Technol. 2010; 4(2):404-18.

24. Keenan D B, Mastrototaro J J, Voskanyan, Steil G. Delays in Minimally Invasive Continuous Glucose Monitoring Devices: A Review of Current Technology. J Diabetes Sci Technol. 2009; 3(5):1207-14.

25. Kovatchev B P, Gonder-Frederick L A, Cox D J, Clarke W L. Evaluating the accuracy of continuous glucose-monitoring sensors: continuous glucose-error grid analysis illustrated by TheraSense Freestyle Navigator data. Diabetes Care. 2004; 27(8):1922-8.

26. Facchinetti A, Sparacino G, Cobelli C. Reconstruction of glucose in plasma from interstitial fluid continuous glucose monitoring data: role of sensor calibration. J Diabetes Sci Technol. 2007; 1 (5):617-23.

27. De Nicolao G, Sparacino G, Cobelli C. Nonparametric input estimation in physiological systems: problems, methods and case study. Automatica. 1997; 33:851-70.

APPENDIX B

The devices, systems, non-transitory computer readable medium, and methods of various embodiments of the invention disclosed herein may utilize aspects disclosed in the following references, applications, publications and patents and which are hereby incorporated by reference herein in their entirety (and which are not admitted to be prior art with respect to the present invention by inclusion in this section):

A. International Patent Application No. PCT/US2014/045393 entitled "Simulation of Endogenous and Exogenous Glucose/Insulin/Glucagon interplay in Type 1 Diabetic Patients," filed Jul. 3, 2014.

B. U.S. patent application Ser. No. 14/266,612 entitled "Method, System and Computer Program Product for Real-Time Detection of Sensitivity Decline in Analyte Sensors," filed Apr. 30, 2014.

C. U.S. patent application Ser. No. 13/418,305 entitled "Method, System and Computer Program Product for Real-Time Detection of Sensitivity Decline in Analyte Sensors," filed Mar. 12, 2012; U.S. Pat. No. 8,718,958, issued May 6, 2014.

D. International Patent Application No. PCT/US2007/082744 entitled "Method, System and Computer Program Product for Real-Time Detection of Sensitivity Decline in Analyte Sensors," filed Oct. 26, 2007.

E. U.S. patent application Ser. No. 11/925,689 entitled "Method, System and Computer Program Product for Real-Time Detection of Sensitivity Decline in Analyte Sensors," filed Oct. 26, 2007; U.S. Pat. No. 8,135,548, issued Mar. 13, 2012.

F. U.S. patent application Ser. No. 14/241,383 entitled "Method, System and Computer Readable Medium for Adaptive Advisory Control of Diabetes," filed Feb. 26, 2014.

G. International Patent Application No. PCT/US2012/052422 entitled "Method, System and Computer Readable Medium for Adaptive Advisory Control of Diabetes," filed Aug. 26, 2012.

H. International Patent Application No. PCT/US2014/017754 entitled "Method and System for Model-Based Tracking of Changes in Average Glycemia in Diabetes," filed Feb. 21, 2014.

I. U.S. patent application Ser. No. 14/128,922 entitled "Unified Platform for Monitoring and Control of Blood Glucose Levels in Diabetic Patients," filed Dec. 23, 2013.

J. International Patent Application No. PCT/US2012/043910 entitled "Unified Platform for Monitoring and Control of Blood Glucose Levels in Diabetic Patients," filed Jun. 23, 2012.

K. U.S. patent application Ser. No. 14/128,811 entitled "Methods and Apparatus for Modular Power Management and Protection of Critical Services in Ambulatory Medical Devices," filed Dec. 23, 2013.

L. International Patent Application No. PCT/US2012/043883 entitled "Methods and Apparatus for Modular Power Management and Protection of Critical Services in Ambulatory Medical Devices," filed Jun. 22, 2012.

M. U.S. patent application Ser. No. 29/467,039 entitled "Alarm Clock Display of Personal Blood Glucose Level," filed Sep. 13, 2013.

N. U.S. patent application Ser. No. 14/015,831 entitled "CGM-Based Prevention of Hypoglycemia via Hypoglycemia Risk Assessment and Smooth Reduction Insulin Delivery," filed Aug. 30, 2013.

O. U.S. patent application Ser. No. 13/203,469 entitled "CGM-Based Prevention of Hypoglycemia via Hypoglycemia Risk Assessment and Smooth Reduction Insulin Delivery," filed Aug. 25, 2011; U.S. Pat. No. 8,562,587, issued Oct. 22, 2013.

P. International Patent Application No. PCT/US2010/025405 entitled "CGM-Based Prevention of Hypoglycemia via Hypoglycemia Risk Assessment and Smooth Reduction Insulin Delivery," filed Feb. 25, 2010.

Q. International Patent Application No. PCT/US2013/053664 entitled "Method, System, and Computer Simulation for Testing and Monitoring of Treatment Strategies for Stress Hyperglycemia in the ICU," filed Aug. 5, 2013.

R. U.S. patent application Ser. No. 13/637,359 entitled "Method, System, and Computer Program Product for Improving the Accuracy of Glucose Sensors Using Insulin Delivery Observation in Diabetes," filed Sep. 25, 2012; U.S. Patent Application Publication No. 2013/0079613, Mar. 28, 2013.

S. International Patent Application No. PCT/US2011/029793 entitled "Method, System, and Computer Program Product for Improving the Accuracy of Glucose Sensors Using Insulin Delivery Observation in Diabetes," filed Mar. 24, 2011.

T. U.S. patent application Ser. No. 13/634,040 entitled "Method and System for the Safety, Analysis, and Supervision of Insulin Pump Action and Other Modes of Insulin Delivery in Diabetes," filed Sep. 11, 2012; U.S. Patent Application Publication No. 2013/0116649, May 9, 2013.

U. International Patent Application No. PCT/US2011/028163 entitled "Method and System for the Safety, Analysis, and Supervision of Insulin Pump Action and Other Modes of Insulin Delivery in Diabetes," filed Mar. 11, 2011.

V. U.S. patent application Ser. No. 13/394,091 entitled "Tracking the Probability for Imminent Hypoglycemia in Diabetes from Self-Monitoring Blood Glucose (SMBG) Data," filed Mar. 2, 2012; U.S. Patent Application Publication No. 2012/0191361, Jul. 26, 2012.

W. International Patent Application No. PCT/US2010/047711 entitled "Tracking the Probability for Imminent Hypoglycemia in Diabetes from Self-Monitoring Blood Glucose (SMBG) Data," filed Sep. 2, 2010.

X. U.S. patent application Ser. No. 13/393,647 entitled "System, Method and Computer Program Product for Adjustment of Insulin Delivery (AID) in Diabetes Using Nominal Open-Loop Profiles," filed Mar. 1, 2012; U.S. Patent Application Publication No. 2012/0245556, Sep. 27, 2012.

Y. International Patent Application No. PCT/US2010/047386 entitled "System, Method and Computer Program Product for Adjustment of Insulin Delivery (AID) in Diabetes Using Nominal Open-Loop Profiles," filed Aug. 31, 2010.

Z. U.S. patent application Ser. No. 13/380,839 entitled "System, Method, and Computer Simulation Environment for in Silico Trials in Pre-Diabetes and Type 2 Diabetes," filed Dec. 25, 2011; U.S. Patent Application Publication No. 2012/0130698, May 24, 2012.

AA. International Patent Application No. PCT/US2010/040097 entitled "System, Method, and Computer Simulation Environment for in Silico Trials in Prediabetes and Type 2 Diabetes," filed Jun. 25, 2010.

BB. U.S. patent application Ser. No. 13/322,943 entitled "System Coordinator and Modular Architecture for Open-Loop and Closed-Loop Control of Diabetes," filed Nov. 29, 2011; U.S. Patent Application Publication No. 2012/0078067, Mar. 29, 2012.

CC. International Patent Application No. PCT/US2010/036629 entitled "System Coordinator and Modular Architecture for Open-Loop and Closed-Loop Control of Diabetes," filed May 28, 2010.

DD. U.S. patent application Ser. No. 13/131,467 entitled "Method, System, and Computer Program Product for Tracking of Blood Glucose Variability in Diabetes," filed May 26, 2011; U.S. Patent Application Publication No. 2011/0264378, Oct. 27, 2011.

EE. International Patent Application No. PCT/US2009/065725 entitled "Method, System, and Computer Program Product for Tracking of Blood Glucose Variability in Diabetes," filed Nov. 24, 2009.

FF. U.S. patent application Ser. No. 12/975,580 entitled "Method, System, and Computer Program Product for the Evaluation of Glycemic Control in Diabetes from Self-Monitoring Data," filed Dec. 22, 2010.

GG. U.S. patent application Ser. No. 11/305,946 entitled "Method, System, and Computer Program Product for the Evaluation of Glycemic Control in Diabetes from Self-Monitoring Data," filed Dec. 19, 2005; U.S. Pat. No. 7,874,985, issued Jan. 25, 2011.

HH. U.S. patent application Ser. No. 10/240,228 entitled "Method, System, and Computer Program Product for the Evaluation of Glycemic Control in Diabetes from Self-Monitoring Data," filed Sep. 26, 2002; U.S. Pat. No. 7,025,425, issued Apr. 11, 2006.

II. International Patent Application No. PCT/US2001/009884 entitled "Method, System, and Computer Program Product for the Evaluation of Glycemic Control in Diabetes," filed Mar. 29, 2001.

JJ. U.S. patent application Ser. No. 12/674,348 entitled "Method, Computer Program Product and System for individual Assessment of Alcohol Sensitivity," filed Feb. 19, 2010.

KK. International Patent Application No. PCT/US2008/073738 entitled "Method, Computer Program Product and System for individual Assessment of Alcohol Sensitivity," filed Aug. 20, 2008.

LL. U.S. patent application Ser. No. 12/665,149 entitled "Method, System and Computer Program Product for Evaluation of Insulin Sensitivity, Insulin/Carbohydrate Ratio, and Insulin Correction Factors in Diabetes from Self-Monitoring Data," filed Dec. 17, 2009.

MM. International Patent Application No. PCT/US2008/069416 entitled "Method, System and Computer Program Product for Evaluation of Insulin Sensitivity, Insulin/Carbohydrate Ratio, and Insulin Correction Factors in Diabetes from Self-Monitoring Data," filed Jul. 8, 2008.

NN. U.S. patent application Ser. No. 12/664,444 entitled "Method, System and Computer Simulation Environment for Testing of Monitoring and Control Strategies in Diabetes," filed Dec. 14, 2009.

OO. International Patent Application No. PCT/US2008/067725 entitled "Method, System and Computer Simulation Environment for Testing of Monitoring and Control Strategies in Diabetes," filed Jun. 20, 2008.

PP. U.S. patent application Ser. No. 12/516,044 entitled "Method, System, and Computer Program Product for the Detection of Physical Activity by Changes in Heart Rate, Assessment of Fast Changing Metabolic States, and applications of Closed and Open Control Loop in Diabetes," filed May 22, 2009; U.S. Pat. No. 8,585,593, issued Nov. 19, 2013.

QQ. International Patent Application No. PCT/US2007/085588 entitled "Method, System, and Computer Program Product for the Detection of Physical Activity by Changes in Heart Rate, Assessment of Fast Changing Metabolic States, and Applications of Closed and Open Control Loop in Diabetes," filed Nov. 27, 2007.

RR. U.S. patent application Ser. No. 12/159,891 entitled "Method, System and Computer Program Product for Evaluation of Blood Glucose Variability in Diabetes from Self-Monitoring Data," filed Jul. 2, 2008.

SS. International Patent Application No. PCT/US2007/000370 entitled "Method, System and Computer Program Product for Evaluation of Blood Glucose Variability in Diabetes from Self-Monitoring Data," filed Jan. 5, 2007.

TT. U.S. patent application Ser. No. 12/139,976 entitled "Method, Apparatus and Computer Program Product for Assessment of Attentional Impairments," filed Jun. 16, 2008; U.S. Pat. No. 8,340,752, issued Dec. 25, 2012.

UU. U.S. patent application Ser. No. 10/476,826 entitled "Method, Apparatus, and Computer Program Product for Assessment of Attentional Impairments," filed Nov. 3, 2003; U.S. Pat. No. 7,403,814, issued Jul. 22, 2008.

VV. International Patent Application No. US02/14188 entitled "Method, Apparatus, and Computer Program Product for Assessment of Attentional Impairments," filed May 6, 2002.

WW. U.S. patent application Ser. No. 12/065,257 entitled "Accuracy of Continuous Glucose Sensors," filed Feb. 28, 2008; U.S. Patent Application Publication No. 2008/0314395, Dec. 25, 2008.

XX. International Patent Application No. PCT/US2006/033724 entitled "Method for Improvising Accuracy of Continuous Glucose Sensors and a Continuous Glucose Sensor Using the Same," filed Aug. 29, 2006.

YY. U.S. patent application Ser. No. 11/943,226 entitled "Systems, Methods and Computer Program Codes for Recognition of Patterns of Hyperglycemia and Hypoglycemia, increased Glucose Variability, and ineffective Self-Monitoring in Diabetes," filed Nov. 20, 2007; U.S. Patent Application Publication No. 2008/0154513, Jun. 26, 2008.

ZZ. U.S. patent application Ser. No. 11/578,831 entitled "Method, System and Computer Program Product for Evaluating the Accuracy of Blood Glucose Monitoring Sensors/Devices," filed Oct. 18, 2006; U.S. Pat. No. 7,815,569, issued Oct. 19, 2010.

AAA. International Patent Application No. US2005/013792 entitled "Method, System and Computer Program Product for Evaluating the Accuracy of Blood Glucose Monitoring Sensors/Devices," filed Apr. 21, 2005.

BBB. U.S. patent application Ser. No. 10/592,883 entitled "Method, Apparatus, and Computer Program Product for Stochastic Psycho-physiological Assessment of Attentional Impairments," filed Sep. 15, 2006; U.S. Pat. No. 7,761,144, issued Jul. 20, 2010.

CCC. International Patent Application No. US2005/008908 entitled "Method, Apparatus, and Computer Program Product for Stochastic Psycho-physiological Assessment of Attentional Impairments," filed Mar. 17, 2005.

DDD. U.S. patent application Ser. No. 10/524,094 entitled "Method, System, and Computer Program Product for the Processing of Self-Monitoring Blood Glucose (SMBG) Data To Enhance Diabetic Self-Management," filed Feb. 9, 2005; U.S. Pat. No. 8,538,703, issued Sep. 17, 2013.

EEE. International Patent Application No. PCT/US2003/025053 entitled "Managing and Processing Self-Monitoring Blood Glucose," filed Aug. 8, 2003.

FFF. International Patent Application No. PCT/US2002/005676 entitled "Method and Apparatus for the Early Diagnosis of Subacute, Potentially Catastrophic Illness," filed Feb. 27, 2002.

GGG. U.S. patent application Ser. No. 09/793,653 entitled "Method and Apparatus for the Early Diagnosis of Subacute, Potentially Catastrophic Illness," filed Feb. 27, 2001; U.S. Pat. No. 6,804,551, issued Oct. 12, 2004.

HHH. U.S. patent application Ser. No. 10/069,674 entitled "Method and Apparatus for Predicting the Risk of Hypoglycemia," filed Feb. 22, 2002; U.S. Pat. No. 6,923,763, issued Aug. 2, 2005.

III. International Patent Application No. US00/22886 entitled "Method and Apparatus for Predicting the Risk of Hypoglycemia," filed Aug. 21, 2000.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the disclosure, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

The invention claimed is:

1. A method for improving the accuracy of a continuous glucose monitoring system (CGM) comprising:

obtaining an output CGM signal at a time t from a CGM device;

removing, substantially in real time, random noise from said CGM signal by estimating a value of the CGM signal at a time t+PH using a noise state estimation, wherein:

PH is a real-time short-time prediction horizon selected based, at least in part, on blood glucose-to-interstitial glucose (BG-to-IG) kinetics; and the noise state estimation is based on a noise-estimation algorithm developed in a stochastic context and implemented using a Kalman filter, wherein one or more unknown parameters within the Kalman filter are estimated by using a Bayesian smoothing criterion;

substituting in real time the estimated value of the CGM signal at time t+PH for the output CGM signal at time t;

using the estimated value of the CGM signal at time t+PH as the true value of the CGM signal at time t.

2. The method according to claim 1, comprising:
using a prediction horizon PH of less than 20 minutes.

3. The method according to claim 2, comprising:
compensating part of a delay introduced by low-pass characteristic of a blood glucose-to-interstitial (BG-to-IG) kinetic system.

4. The method according to claim 1, comprising:
compensating part of a delay introduced by a low-pass characteristic of a blood glucose-to-interstitial (BG-to-IG) kinetic system.

5. The method according to claim 1, comprising:
substituting a current CGM value given in output by a CGM sensor at time t, named CGM (t), with the glucose concentration predicted by the noise-estimation algorithm PH minutes ahead in time.

6. The method according to claim 1, wherein the PH is a value that matches that of a diffusion constant of blood glucose-to-interstitial glucose (BG-to-IG) kinetics for the CGM device, wherein the estimated value of the CGM signal at time t+PH is a closer approximation of blood glucose than the output CGM signal at time t.

7. The method according to claim 1, wherein the one or more unknown parameters are variance of the process and/or measurement noise.

8. A method for improving the accuracy of a continuous glucose monitoring (CGM) sensor comprising:

improving accuracy of CGM readings by reducing random noise and calibration errors in said readings using a real-time short-time prediction horizon (PH); and denoising said CGM readings by using a Kalman filter (KF) coupled with a Bayesian smoothing criterion for the estimation of its unknown parameters, wherein the estimation of unknown parameters via the KF provides the short-time prediction;

wherein the PH is a value that matches that of a diffusion constant of blood glucose-to-interstitial glucose (BG-to-IG) kinetics for the CGM sensor, wherein an estimated value of a CGM signal at time t+PH is a closer approximation of blood glucose than an output CGM signal at time t.

9. A system for improving the accuracy of a continuous glucose monitoring sensor comprising:

a digital processor;

a continuous glucose monitoring (CGM) sensor in communication with the digital processor, the continuous glucose monitoring (CGM) sensor configured to generate a glucose signal; and a denoising module, configured to receive the glucose signal from the continuous glucose monitoring (CGM) sensor, and generate an improved accuracy CGM signal by reducing random noise and calibration errors using a real-time short-time glucose prediction horizon (PH) to estimate the real time denoised value of the CGM signal based on a noise-estimation algorithm developed in a stochastic context and implemented using a Kalman filter;

wherein the PH is a value that matches that of a diffusion constant of blood glucose-to-interstitial glucose (BG-to-IG) kinetics for the CGM sensor, wherein an estimated value of a CGM signal at time t+PH is a closer approximation of blood glucose than an output CGM signal at time t.

10. The system according to claim 9, wherein the denoising module is configured to use a prediction horizon PH of less than 20 minutes.

11. The system according to claim 9, wherein the denoising module is configured to compensate part of a delay introduced by a low-pass characteristic of a blood glucose-to-interstitial (BG-to-IG) kinetic system.

12. The system according to claim 9, wherein the denoising module is configured to substitute a current CGM value given in output by a CGM sensor at time t, named CGM (t), with the glucose concentration predicted by the noise-estimation algorithm PH minutes ahead in time.

13. The system according to claim 12, wherein a Bayesian smoothing criterion is coupled with the Kalman Filter for estimation of unknown parameters.

14. The system according to claim 12, wherein the noise-estimation algorithm uses CGM data only for real-time application.

15. The system according to claim 9, wherein a Bayesian smoothing criterion is coupled with the Kalman Filter for estimation of unknown parameters.

16. The system according to claim 9, wherein the noise-estimation algorithm uses CGM data only for real-time application.

17. A method of increasing accuracy of a continuous glucose monitoring (CGM) sensor signal measured at a time t, by using a short-time prediction horizon (PH) to estimate a value of a CGM signal at time t+PH by applying CGM data obtained at time t to a Kalman filter for time t+PH, and substituting the estimated value of CGM signal at time t+PH for the real time CGM signal value obtained at time t, wherein the estimated value of CGM signal is determined using a noise state estimation based on a noise-estimation algorithm developed in a stochastic context, wherein the PH is a value that matches that of a diffusion constant of blood glucose-to-interstitial glucose (BG-to-IG) kinetics for the CGM sensor, wherein an estimated value of a CGM signal at time t+PH is a closer approximation of blood glucose than an output CGM signal at time t.

* * * * *